US010258066B2

(12) United States Patent
Tang et al.

(10) Patent No.: US 10,258,066 B2
(45) Date of Patent: Apr. 16, 2019

(54) MICROWAVE STERILIZATION OR PASTEURIZATION TRANSPORT CARRIERS AND SYSTEM

(71) Applicant: Washington State University, Pullman, WA (US)

(72) Inventors: Juming Tang, Pullman, WA (US); Fang Liu, Pullman, WA (US)

(73) Assignee: Washington State University, Pullman, WA (US)

(*) Notice: Subject to any disclaimer, the term of this patent is extended or adjusted under 35 U.S.C. 154(b) by 162 days.

(21) Appl. No.: 15/212,655

(22) Filed: Jul. 18, 2016

(65) Prior Publication Data

US 2018/0014559 A1    Jan. 18, 2018

(51) Int. Cl.
| | | |
|---|---|---|
| A23L 3/00 | (2006.01) | |
| A23L 3/01 | (2006.01) | |
| A61L 2/12 | (2006.01) | |
| A61L 2/26 | (2006.01) | |

(52) U.S. Cl.
CPC ............. *A23L 3/01* (2013.01); *A23L 3/001* (2013.01); *A61L 2/12* (2013.01); *A61L 2/26* (2013.01)

(58) Field of Classification Search
CPC ..... A23L 3/00; A23L 3/01; A23L 3/02; A23L 3/04; A23L 3/06; A23L 3/08; A23L 3/18; A23L 3/20
USPC ................. 99/451, 483; 219/700, 770, 771
See application file for complete search history.

(56) References Cited

U.S. PATENT DOCUMENTS

| | | | | |
|---|---|---|---|---|
| 3,335,253 A * | 8/1967 | Harper | ...................... | A23L 3/01 |
| | | | | 219/700 |
| 3,398,251 A * | 8/1968 | Jeppson | ..................... | A23L 3/01 |
| | | | | 219/686 |
| 4,808,782 A * | 2/1989 | Nakagawa | ................ | A23L 3/01 |
| | | | | 219/701 |
| 4,956,530 A * | 9/1990 | Koch | ....................... | A23L 3/01 |
| | | | | 219/701 |
| 5,066,503 A * | 11/1991 | Ruozi | ..................... | A23L 3/001 |
| | | | | 426/234 |
| 5,298,707 A * | 3/1994 | Sprecher | ................ | H05B 6/782 |
| | | | | 219/693 |
| 5,913,422 A * | 6/1999 | Cote | ......................... | A61L 2/26 |
| | | | | 206/210 |
| 6,198,106 B1 * | 3/2001 | Barney | ..................... | A61J 1/10 |
| | | | | 250/453.11 |
| 6,323,471 B1 * | 11/2001 | Yagi | ..................... | H05B 6/6408 |
| | | | | 219/680 |

(Continued)

*Primary Examiner* — Dana Ross
*Assistant Examiner* — Ayub A Maye
(74) *Attorney, Agent, or Firm* — W & C IP

(57) ABSTRACT

The present embodiments are directed to a processing system and transport carrier components for sterilization or pasteurization. In particular, an example embodiment includes a transport carrier for carrying one or more items to be sterilized or pasteurized, wherein the transport carrier includes a carrier base and one or more cross members coupled to and extending between sides of the carrier base. In addition, the transport carrier includes a tray member configured from at least one material of construction selected from a metal, a metal alloy, and a plastic, wherein the tray member extends between ends along the sides of the carrier base, and wherein the tray member further comprises one or more apertures configured to receive the one or more items to be sterilized or pasteurized.

7 Claims, 16 Drawing Sheets

(56) References Cited

U.S. PATENT DOCUMENTS

| | | | | |
|---|---|---|---|---|
| 6,822,207 B2* | 11/2004 | Schmidt | ............... | A21B 1/48 |
| | | | | 198/804 |
| 6,852,958 B2* | 2/2005 | Germain | ............ | B65D 81/3453 |
| | | | | 219/679 |
| 8,113,190 B2* | 2/2012 | Dougherty | ............... | A21B 1/48 |
| | | | | 126/15 A |
| 8,586,899 B2* | 11/2013 | Mackay | ............... | A23L 3/01 |
| | | | | 198/457.03 |
| 8,878,109 B2* | 11/2014 | Mackay | ............... | H05B 6/782 |
| | | | | 219/678 |
| 9,642,385 B2 | 5/2017 | Tang et al. | | |
| 2004/0104221 A1* | 6/2004 | Kono | ............... | H05B 6/782 |
| | | | | 219/700 |
| 2004/0131519 A1* | 7/2004 | Amedeo | ............... | A23L 3/01 |
| | | | | 422/308 |
| 2005/0127068 A1* | 6/2005 | Tang | ............... | H05B 6/701 |
| | | | | 219/700 |
| 2006/0231550 A1* | 10/2006 | Wendel | ............... | H05B 6/782 |
| | | | | 219/700 |

* cited by examiner

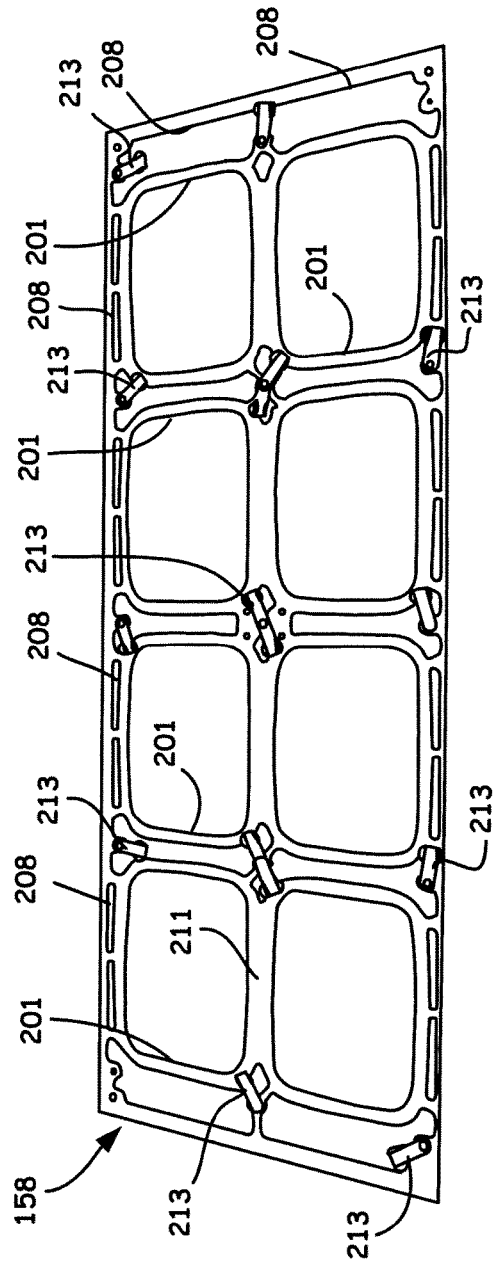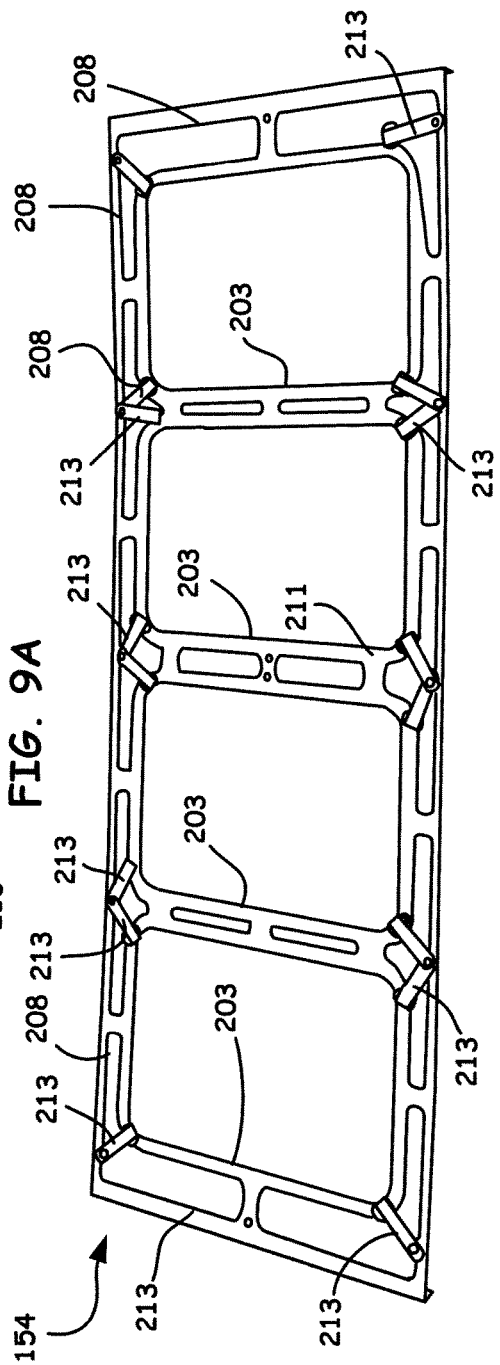
FIG. 9A
FIG. 9B

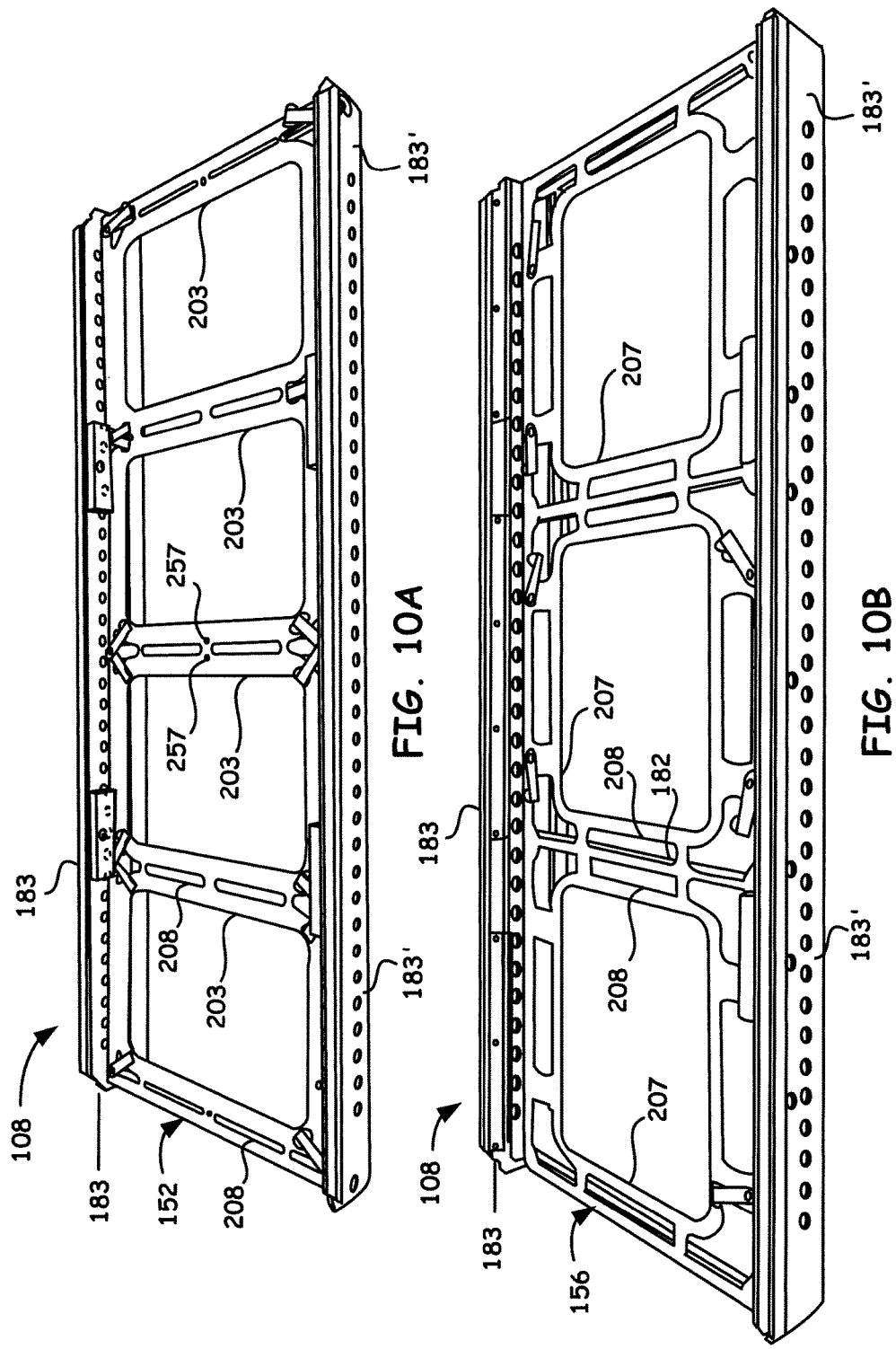

MICROWAVE STERILIZATION OR PASTEURIZATION TRANSPORT CARRIERS AND SYSTEM

STATEMENT REGARDING FEDERALLY SPONSORED RESEARCH

This invention was made with government support under 2016-68003-24840 awarded by The United States Department of Agriculture, under the National Institute of Food and Agriculture. The government has certain rights in this invention.

BACKGROUND OF THE INVENTION

Field of the Invention

The present embodiments herein relate to microwave systems for heating one or more items, articles, and/or loads, and in particular, to food transport carriers having coupled tray designs configured to be easily interchanged for receiving food items configured with different sizes and shapes.

Discussion of the Related Art

Sterilization or pasteurization has been used in preserving foods, preventing sepsis in humans and animals, and in other fields. For example, food products can be sterilized or pasteurized to reduce or eliminate fungi, bacteria, viruses, spore forms, or other harmful microbiological organisms that may cause spoilage or even food-borne diseases. One sterilization or pasteurization technique includes heating food products with hot air, hot water, or steam. Heating in such a manner, however, can result in poor taste, texture, color, or smell of the food products. Also, such heating techniques can be energy inefficient and may require long processing times.

Moreover, transport carriers for the food items in industrial microwave systems have not addressed in an efficient and robust manner, the ability to handle items (e.g., food pouches) of different sizes and different aspect shapes in a secured manner and that aids in efficient coupling of the directed energy to the desired items as they move through the heating cavities. Background information on a transport carrier to be used in a processing system as disclosed herein, is described in U.S. Patent Application Publication No. 2016/0029685, entitled: "Microwave Sterilization for Pasteurization," to Tang et al., filed Oct. 14, 2015, the disclosure of which is incorporated by reference in its entirety. In particular, part of the disclosure for U.S. Patent Application Publication No. 2016/0029685 includes the following: "FIG. 7A is a perspective view of an example transport carrier 108 suitable for the processing system 100 of FIG. 1 in accordance With embodiments of the disclosed technology. As shown in FIG. 7A, the transport carrier 108 can include a carrier base 180 carrying one or more cross members 182. The carrier base 180 can have any suitable shape based on at least one of a shape or size of the items 101 (FIG. 1) to be carried thereon. For example, in the illustrated embodiment, the carrier base 180 has a generally rectilinear shape with a first side 181 *a* and a second side 181 *b* (collectively referred to as side or sides 181) extending between a first end 180 *a* and a second end 180 *b* of the base 180. In other embodiments, the carrier base 180 can have a generally oval, square, and/or other suitable shapes. As shown in FIG. 7A, the first and second sides 181 *a* and 181 *b* each include a perforated plate 185 having a first support 184 and a second support 186 extending away from the perforated plate 185. The first support 184 extends toward an interior region of the carrier base ISO, and the second support 186 extends in a direction opposite of the first support 184. Both the first and second supports 184 and 186 extend transversely between the first end 180 *a* and the second end 180 *b*. The first support 184 may be configured to support one or more items 101 carried in the transport carrier 108. The second support 186 may be configured to engage the rollers 122 (FIG. 1) or other suitable components of the processing system 100. The first and second ends 180 *a* and 180 *b* include one or more end bars 183 (three are shown at each end for illustration purposes). In other embodiments, the first and second ends 180 *a* and 180 *b* can include the cross members 182 instead."

Accordingly, a need exists for an improved microwave industrial system transport carrier. The present embodiments address such a need via a novel transport carrier design, as disclosed herein, that utilizes trays (e.g., plates) comprised substantially of metal/metal alloys and or other materials configured to receive varying shaped pouches. Such an overall design enables efficient coupling of energy to the food trays, as well as uniform, short heating times.

SUMMARY OF THE INVENTION

It is to be appreciated that the present example embodiments herein are directed to pasteurization or sterilization systems and components. One aspect includes a transport carrier for carrying one or more items to be sterilized or pasteurized, the transport carrier comprising: a carrier base having a first end opposite a second end and a first side opposite a second side, wherein the first side and the second side extends between the first end and the second end; one or more cross members coupled to and extending between the first side and the second side of the carrier base; and a tray member comprising at least one material of construction selected from a metal, a metal alloy, and a plastic, wherein the tray member extends between the first end and the second end and along the first side and the second side, and wherein the tray member further comprises one or more apertures configured to receive one or more items to be sterilized or pasteurized.

Another aspect of the embodiments herein is directed to a processing system for sterilization or pasteurization of one or more items that includes: a transport carrier for carrying the one or more items, wherein the transport carrier further comprises: a carrier base having a first end opposite a second end and a first side opposite a second side, wherein the first side and the second side extends between the first end and the second end; one or more cross members coupled to and extending between the first side and the second side of the carrier base; and a tray member comprising at least one material of construction selected from a metal, a metal alloy, and a plastic, wherein the tray member extends between the first end and the second end and along the first side and the second side, and wherein the tray member further comprises one or more apertures configured to receive one or more items to be sterilized or pasteurized; a transport unit having a channel extending between a third end and a fourth end and between a third side and a fourth side, wherein the transport unit further includes an inlet and an outlet configured to receive the transport carrier at the inlet in a disposed manner and move the transport carrier along a direction from the third end to the fourth end to the outlet for further processing, and wherein the transport unit is further configured to allow an immersion fluid to circulate in the channel of the transport unit; and a microwave assembly coupled to the transport unit, wherein the microwave assembly is configured to apply microwave energy to the one or more items while the one or more items are immersed in the circulated immersion fluid and subject to a hydrostatic pressure and while the one or more items are moving along the direction from the third end to the fourth end as provided by the transport carrier disposed within the transport unit, and wherein the hydrostatic pressure of the immersion fluid prevents the water content of the item from causing steam explosion in the item while the microwave energy is applied.

Accordingly, the embodiments herein provide for robust, easy to load and unload food trays, wherein a carrier can be configured to receive the trays having different size and shapes of apertures modified for differing food pouches. Such designs enable efficient coupling of energy to the food trays, relative uniform heating, and short heating times as the disposed carriers with food trays move through the disclosed microwave sections.

BRIEF DESCRIPTION OF THE DRAWINGS

FIG. 9A shows a top perspective view of a tray design for holding a plurality of 8 ounce food items, as disclosed herein.

FIG. 9B shows a top perspective view of a tray design for holding a plurality of 10 ounce food items, as disclosed herein.

FIG. 10A shows a top perspective view of an assembled transport carrier incorporated with an interchangeable tray configured for receiving 16 ounce food items.

FIG. 10B shows a top perspective view of an assembled transport carrier incorporated with an interchangeable tray configured for receiving 6 pound food items.

DETAILED DESCRIPTION

Figure 1:
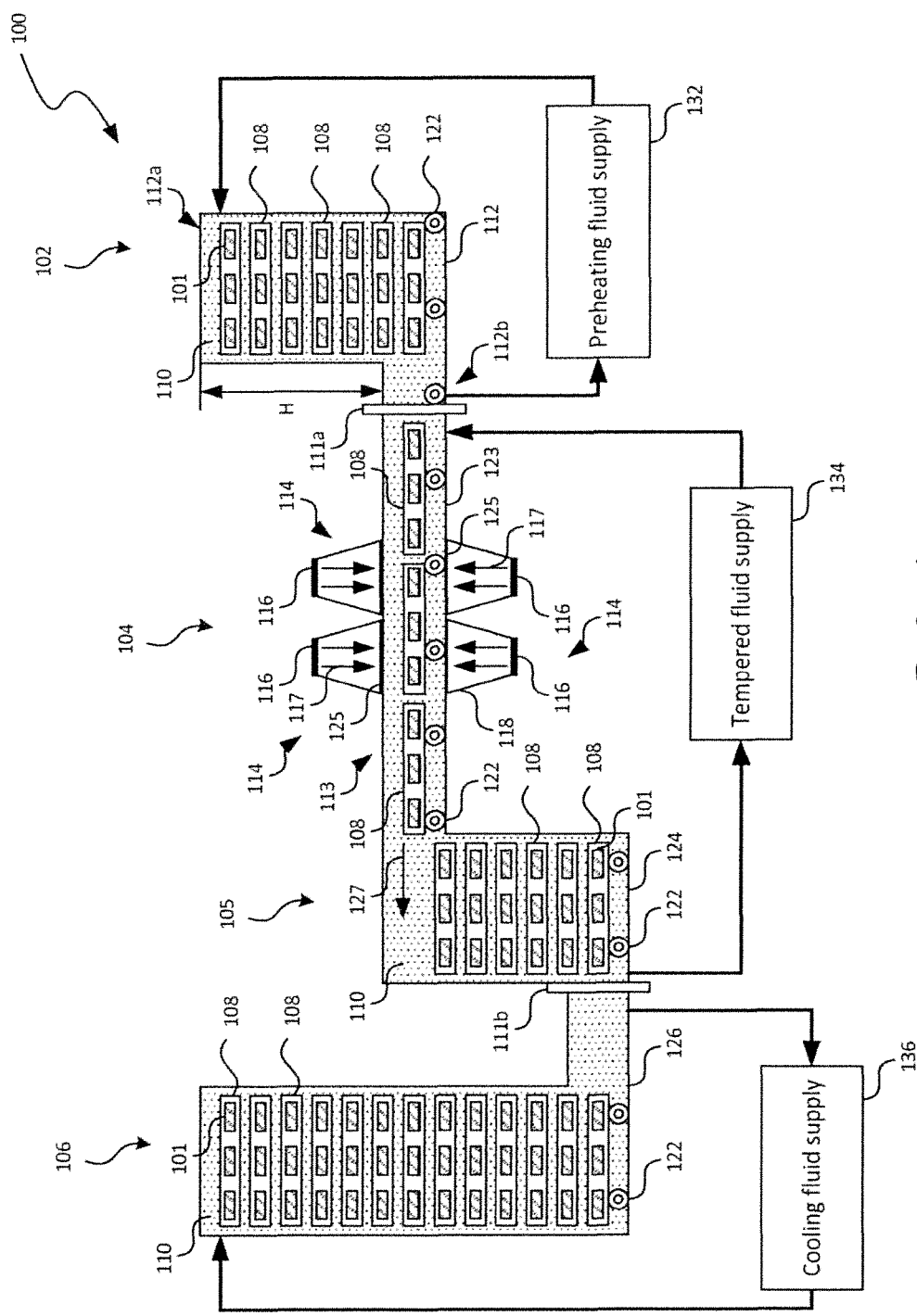
FIG. 1 is a schematic diagram illustrating a processing system useful for sterilization or pasteurization in accordance with embodiments of the disclosed technology.

In the description of the invention herein, it is understood that a word appearing in the singular encompasses its plural counterpart, and a word appearing in the plural encompasses its singular counterpart, unless implicitly or explicitly understood or stated otherwise. Furthermore, it is understood that for any given component or embodiment described herein, any of the possible candidates or alternatives listed for that component may generally be used individually or in combination with one another, unless implicitly or explicitly understood or stated otherwise. It is to be noted that as used herein, the term "adjacent" does not require immediate adjacency. Moreover, it is to be appreciated that the figures, as shown herein, are not necessarily drawn to scale, wherein some of the elements may be drawn merely for clarity of the invention. Also, reference numerals may be repeated among the various figures to show corresponding or analogous elements. Additionally, it will be understood that any list of such candidates or alternatives is merely illustrative, not limiting, unless implicitly or explicitly understood or stated otherwise.

In addition, unless otherwise indicated, numbers expressing quantities of ingredients, constituents, reaction conditions and so forth used in the specification and claims are to be understood as being modified by the term "about." Accordingly, unless indicated to the contrary, the numerical parameters set forth in the specification and attached claims are approximations that may vary depending upon the desired properties sought to be obtained by the subject matter presented herein. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the subject matter presented herein are approximations, the numerical values set forth in the specific examples are reported as precisely as possible. Any numerical values, however, inherently contain certain errors necessarily resulting from the standard deviation found in their respective testing measurements.

General Description

When microwaves propagate from air to foods, a portion of the waves is reflected; the rest enters the foods. The direction of the entered waves differs (refracted) from the original direction based on fundamental optical principles, as known to those of ordinary skill in the art. The frequency of those waves in foods remains the same as that of the incident waves, whereas the wavelength is shortened by a factor of 6 to 9 in high moisture foods. The propagation direction of the refracted waves is determined by the intrinsic impedances of air and foods according to Snell's law:

$$\Psi = \frac{\eta \sin\theta}{\eta_o} \quad (1)$$

where $\Psi$ is the angle of refraction, $\theta$ is the angle of incidence, $$\eta_o = \frac{\sqrt{\mu_o}}{\sqrt{\epsilon_o}}$$

is the intrinsic impedance of air (377Ω), $$\mu_o = 4\pi \times 10^{-7} \frac{H}{m}$$

is the permeability (determining material's ability to support a magnetic field) of free space, and $$\varepsilon_o = 4\pi \times 10^{-7} \frac{H}{m}$$

is me permittivity (measuring reaction of a material to formation of an electric field) of free space $$\varepsilon_o = 8.854 \times 10^{-12} \frac{F}{m}$$

is the permittivity (measuring reaction of a material to formation of an electric field) of free space. The intrinsic impedance, η in a material is defined as:

$$\eta = \frac{\sqrt{\mu}}{\sqrt{\varepsilon \varepsilon_o}} == \frac{\sqrt{\eta_o}}{\sqrt{\varepsilon}} \quad (2)$$

where μ and ∈ are the permeability and permittivity of foods, respectively. Because foods do not interact with magnetic fields, μ is assumed=$\mu_o$.

The reflected portion of the waves at the food surface is in turn determined by the reflected and refracted angles, as well as the intrinsic properties of the air and the food:

$$\Gamma = \frac{P_r}{P_i} = \frac{\eta_o \cos\Psi - \eta \cos\phi}{\eta_o \cos\Psi + \eta \cos\phi} \quad (3)$$

where $P_r$ is the reflected power and $P_i$ is the incident power.

From such above equations, it is to be noted that more microwave power is reflected from water than for ice because the intrinsic impedance of water is larger than ice. Correspondingly, because high moisture foods have impedance similar to that of water, and frozen foods have intrinsic impedance similar to that of ice, in a single pass, more microwave power is reflected from moist foods than from frozen foods. Also to be noted is that large differences between the impedance of air ($\eta_o$=377) and that of moist foods ($\eta$<60) are also responsible for the edge heating of packaged foods when heated in domestic microwave ovens.

Another important consideration is that because the magnetic component does not interact with foods; only the electric component causes heating. Thus, dielectric properties (electric permittivity) are among the most important characteristics of foods related to microwave heating. These properties are described by the complete relative electric permittivity ∈* (relative to that of air):

$$\in^* = \in' - j\in'' \quad (4)$$

where $j=\sqrt{-1}$. Dielectric constant ∈' expresses the ability of the material to store electric energy and the dielectric loss factor ∈'' determines the conversion of microwave energy into thermal energy:

$$Q = 2\pi \in_o \in'' E^2 \quad (5)$$

where Q is the converted thermal energy per unit volume (w/m³) and E (V/m) is the electric field instantaneous intensity. Moreover, the dielectric properties of foods are affected by food composition, in particular moisture content, salt, and fat content. They also depend on temperature and frequency.

Another important factor considered in the novel design parameters for the system herein is that microwaves at 915 MHz penetrate deeply in tap and deionized water, in particular at elevated temperatures (for example, >150 mm at 120° C.). Thus, tap water at elevated temperatures is relatively transparent to 915 MHz microwaves.

Accordingly, the present embodiments herein include two unique design features that take in all of the considerations discussed above: (1) 915 MHz single-mode cavities and (2) water immersion. 915 MHz microwaves have adequate wavelength for single-mode cavities to accommodate single-meal portion food packages. This is impossible with current 2450 MHz microwaves. In addition, microwaves at 915 MHz penetrate deeper, thus allowing heating of thicker packaged foods. Importantly, instead of heating packaged foods in air which causes severe microwave edge heating, food packages in the system disclosed are heated in a shallow bed of water at high temperatures. Therefore, not only do microwaves at 915 MHz penetrate deeply into water at 80 to 120° C., but because the similarity between the dielectric constant of water and of foods reduces reflection and refraction of microwaves at the interface between water and foods, edge heating of the food items utilized herein is reduced or eliminated.

The overall result using water immersion in addition to other disclosed aspects, is a more stable Q factor (lower Q) (i.e., reduced overheating problems), less reflectivity based on impedance matching and, reduced or eliminated edge heating of the food items. Couple all of the above with the use of the novel metal transport carriers/tray carriers disclosed herein, which surprisingly reduces reflectivity and enhances uniform heating, and one has a very beneficial and novel system that addresses many industrial concerns with respect to sterilization and pasteurization of food components.

Specific Description

FIG. 1 is a schematic diagram illustrating a processing system 100 useful for sterilization or pasteurization of items 101 (e.g., a food product) contained in transport carriers 108 in accordance with embodiments of the disclosed technology. As shown in FIG. 1, the processing system 100 can include a preheating section 102, a heating section 104, and a cooling section 106 (collectively referred to as "sections") coupled to one another in series. In the illustrated embodiment, the processing system 100 also includes an optional holding section 105 between the heating section 104 and the cooling section 106. In other embodiments, the optional holding section 105 may have other suitable configurations, one example of which is described in more detail below with reference to FIG. 6. In further embodiments, the holding section 105 may be eliminated. Even though certain components or sections are illustrated in FIG. 1, the processing system 100 can also include additional and/or different components. For example, the processing system 100 can also include a process logic controller, pneumatic lifts, strainers, filters, sensors (e.g., level sensors, flow meters, pressure gauges, etc.), and/or other suitable mechanical/electrical components.

As shown in FIG. 1, the sections may be configured to circulate and/or hold an immersion fluid 110. In certain embodiments, the immersion fluid 110 can include water, and one or more of the sections may be coupled to a corresponding fluid supplies. For example, the preheating section 102 can be coupled to a preheating fluid supply 132. The cooling section 106 is coupled to a cooling fluid supply 136. In the illustrated embodiment, the heating section 104 and the optional holding section 105 are both coupled to a tempered fluid supply 134. In other embodiments, the heating section 104 and the optional holding section 105 may each be coupled to a corresponding tempered fluid supplies (not shown).

Each of the fluid supplies 132, 136, and 138 can be configured to provide and circulate the immersion fluid 110 at an operating temperature. For example, in certain embodiments, the preheating fluid supply 132 can provide and circulate the immersion fluid 110 at a temperature approximately equal to or above a preheating temperature (e.g., 60° C.) of the items 101 in the preheating section 102. The tempered fluid supply 134 can provide and circulate the immersion fluid 110 at a temperature approximately equal to or above a desired heating temperature (e.g., 90° C.) of the items 101 in the heating section 104. The preheating temperature is generally lower than the heating temperature in the heating section 104. Examples of the heating fluid supply 132, tempered fluid supply 134, and the cooling fluid supply 136 are described in more detail below with reference to FIGS. 5A-5C, respectively. In other embodiments, the immersion fluid 110 may also include fat, oil, polymeric solvents, and/or other suitable fluid in liquid or semi-liquid form.

Also shown in FIG. 1, one or more dividers 111 (shown individually as first divider 111a and second divider 111b) may be configured to controllably isolate the immersion fluid 110 between adjacent sections while allowing the transport carriers 108 to pass through. For example, in the illustrated embodiment, the first divider 111a can controllably isolate the immersion fluid 110 between the preheating section 102 and the heating section 104. The second divider 111b can controllably isolate the immersion fluid 110 between the heating section 104 (and optional holding section 105) and the cooling section 106. In other embodiments, the processing system 100 can also include additional and/or different placement of dividers 111. For example, an additional divider (not shown) may be between the heating section 104 and the holding section 105.

The one or more dividers 111 can each include suitable mechanical and/or electrical components configured to at least partially seal the immersion fluid 110 from flowing to adjacent sections. For example, in one embodiment, a divider 111 can include a pretension door constructed from a flexible material (e.g., rubber), a rigid material (e.g., plastic), or other suitable materials. The pretension door can be normally closed except when allowing the transport carriers 108 to pass through. In another embodiment, a divider 111 can include an actuated gate synchronized with the passing of the transport carriers 108 through the actuated gate. An example of the actuated gate is described below with reference to FIG. 4. In further embodiments, a divider 111 can include other suitable actuated or passive components and/or configurations.

The preheating section 102 is configured to receive one or more of the transport carriers 108 carrying items 101 to be sterilized or pasteurized. The transport carriers 108 are shown in FIG. 1 as each carrying three items 101 for illustration purposes. In other embodiments, the transport carriers 108 can carry two, four, five, six, or any other suitable number of items 101. In one embodiment, the transport carriers 108 may be received in batches. For example, the transport carriers 108 with the items 101 may be loaded into the preheating section 102 before sterilization or pasteurization processing is started and reloaded once the processing of a previous batch is finished. In other embodiments, the transport carriers 108 may be received in a continuous manner from, for example, a conveyer belt (not shown), a manual loading dock (not shown), and/or other suitable sources (not shown). In further embodiments, the transport carriers 108 may be received in semi-continuous or other suitable manners.

The preheating section 102 is also configured to homogenize temperatures of the received items 101 in the transport carriers 108 to a preheating temperature. In one embodiment, the preheating temperature can be about 60° C. In other embodiments, the preheating temperature can be 40° C., 50° C., or any other suitable temperatures. In the illustrated embodiment, the immersion fluid 110 supplied by the preheating fluid supply 132 is used to preheat and/or homogenize the temperatures of the items 101 to the preheating temperature. In other embodiments, steam, hot oil, and/or other thermal media may also be used.

In the illustrated embodiment, the preheating section 102 includes a carrier assembly 112 having an inlet 112a and an outlet 112b that is proximate to the first divider 111a. The carrier assembly 112 can include a vessel, tank, cartridge, or other suitable structures. In certain embodiments, the carrier assembly 112 can have a volume sufficient to provide a residence time such that temperatures of the items 101 in the transport carriers 108 can be at least generally homogenized when passing from the inlet 112a to the outlet 112b of the carrier assembly 112. In other embodiments, the carrier assembly 112 can also have other suitable volumes, structures, shapes, or components.

The carrier assembly 112 can also have a height H relative to the heating section 104 to exert a hydrostatic pressure on the items in the heating section 104. As discussed in more detail below, the hydrostatic pressure exerted on the individual items 101 may prevent or at least reduce the risk of steam explosion during heating in the heating section 104. In one embodiment, the height H can be about 5 meters. In other embodiments, the height H can be 4 meters, 6 meters, or any other suitable distances. In any of the foregoing embodiments, the height H may be adjusted based on at least one of (1) a desired heating temperature of the items 101, (2)

a water content of the items 101, (3) a temperature of the immersion fluid 110 in the heating section 104, (4) power of microwave energy delivered to the items 101 in the heating section, or other suitable factors.

The carrier assembly 112 can also include a transport mechanism configured to transfer the individual transport carriers 108 to the heating section 104. As shown in FIG. 1, one example transport mechanism can include one or more rollers 122 proximate the outlet 112b of the carrier assembly 112. The one or more rollers 122 can be configured to carry one of the transport carriers 108 to the heating section 104 through the outlet 112b and via the first divider 111a. One example carrier assembly 112 having rollers 122 is described in more detail below with reference to FIG. 2.

In other embodiments, the rollers 122 may be omitted from the carrier assembly 112. Instead, the carrier assembly 112 may include mechanical movers, fluid jets, compressed gas, and/or other suitable transport mechanisms to transfer the individual transport carriers 108 from the preheating section 102 to the heating section 104. In further embodiments, the preheating section 102 can also include additional and/or different components. For example, the preheating section 102 may include two, three, or other suitable numbers of carrier assemblies (not shown) arranged in series, parallel, or in other suitable manners.

The heating section 102 is configured to apply microwave energy to the items 101 carried in the transport carriers 108 while the items 101 are immersed in the immersion fluid 110 and subject to a hydrostatic pressure of the immersion fluid 110. The applied microwave energy may be sufficient to raise a temperature (e.g., an interior temperature) of the items 101 to or above a target heating temperature sufficient to achieve sterilization or pasteurization. The interior temperature can be a center temperature or a temperature proximate to a central region of the individual items 101. In one embodiment, the target heating temperature can be about 90° C. In other embodiments, the target heating temperature can be 70° C., 80° C., 100° C. or other suitable temperature values.

The heating section 104 can include a transport unit 113 coupled to one or more microwave assemblies 114. The transport unit 113 can be configured to receive the transport carriers 108 carrying the items 101 from the preheating section 102. The transport unit 113 can also be configured to convey the received transport carriers 108 with the items 101 through the heating section 104 to be irradiated by microwave energy from the microwave assemblies 114 (indicated by arrows 117). As shown in FIG. 1, the transport unit 113 includes a transport housing 123, a plurality of rollers 122, and one or more microwave windows 125 in the transport housing 123. The microwave windows 125 can each include an opening with a microwave transmissive component (e.g., a glass or plastic plate). An example transport unit 113 is described in more detail below with reference to FIG. 3.

The microwave assemblies 114 are each configured to apply microwave energy to both sides of the items 101 simultaneously as the individual items 101 carried by the transport carriers 108 are moved through the transport unit 113. As shown in FIG. 1, each microwave assembly 114 includes two sets of a microwave source 116 coupled to a microwave guide 118 on opposite sides of the transport unit 113. The microwave source 116 can include a single-mode microwave source at a particular frequency (e.g., 915 MHz) or other suitable microwave sources. The microwave guide 118 can include a conical, trapezoidal, or other suitable shaped structure configured to direct the microwave energy 117 from the microwave sources 116 to the items 101 via the corresponding microwave windows 125 in the transport unit 113. In FIG. 1, two side-by-side microwave assemblies 114 are shown for illustration purposes. In other embodiments, the heating section 104 can include one, three, or any other suitable number of microwave assemblies 114. In further embodiments, the microwave assemblies 114 can be spaced apart from each other. In yet further embodiments, the microwave assemblies 114 may be in other suitable arrangements.

The optional holding section 105 can be configured to at least approximately maintain the interior temperature of the heated items for a period of time (referred to as a holding time) to facilitate or effectuate sterilization or pasteurization. Without being bound by theory, it is believed that at least partial removal of certain microbiological organisms (e.g., bacteria) requires maintaining the temperature of the items 101 for a period of time. For example, milk may be pasteurized by heating milk to 72° C. for 15 seconds or 63° C. for 30 minutes. In one embodiment, the holding section 105 can include a holding tank 124 with a volume sufficient to provide a residence time that is equal to or above the holding time. The holding tank 124 can also include one or more rollers 122 configured to convey the transport carriers 108 to the cooling section 106. In other embodiments, the holding section 105 can include a holding tank with other suitable structures, volumes, and/or configurations. In the illustrated embodiment, the optional holding section 105 is shown as being at a lower elevation than the heating section 104. In other embodiments, the holding section 105 may be at the same elevation as or higher elevation then the heating section 104. In further embodiments, the holding section 105 may have other suitable arrangements relative to the heating section 104.

The cooling section 106 can be configured to reduce an overall temperature or interior temperature of the heated items 101 to room temperature (e.g., 15° C.) or other suitable temperatures for handling, transporting, and/or storage. As shown in FIG. 1, the cooling section 106 can include a transport vessel 126 with rollers 122 generally similar to the transport vessel 112 of the preheating section 102. In certain embodiments, the transport vessel 126 can have a volume to provide a sufficient residence time to reduce the overall or interior temperature of the items 101 from the heating section 104 and the optional holding section 105. In other embodiments, the transport vessel 126 may be configured to operate in a batch mode, and thus may have any suitable volumes.

In operation, the preheating section 102 receives the items 101 in the transport 108 and heat and/or homogenize temperatures of the items 101 with the immersion fluid 110 to the preheating temperature. The preheating section 102 may be operated in various modes. For example, in one embodiment, the preheating section 102 may be operated in batches. A plurality of transport carriers 108 with corresponding items 101 are initially received at the transport assembly 112. The preheating fluid supply 132 then provides water at a heating temperature (e.g., 80° C.) to heat and/or homogenize temperatures of the items 101 to the preheating temperature. Once the temperatures of the items 101 are generally homogenized, the transport mechanism (e.g., the rollers 122) can be activated to convey each transport carriers 108 to the heating section 104 via the first divider 111a.

In another embodiment, the preheating section 102 may be operated in a generally continuous mode. For example, the preheating fluid supply 132 can first establish circulation of the immersion fluid 110 at a temperature (e.g., 80° C.) in the transport assembly 112. Subsequently, the transport assembly 112 can receive the transport carriers 108 via the inlet 112a. As the transport carriers 108 travels from the inlet 112a toward the outlet 112b, the circulated water can heat and/or homogenize the temperatures of the items 101. Then, the transport mechanism (e.g., the rollers 122) can continuously convey the individual transport carriers 108 to the heating section 104 via the first divider 111a. In further embodiments, the preheating section 102 may be operated in other suitable manners.

The heating section 104 can then receive the items 101 with generally homogenized temperatures from the preheating section 102 and apply additional heat via microwave energy to the items 101. The tempered fluid supply 134 can initially establish a circulation of the immersion fluid 110 in the heating section 104 (and optional holding section 105). The transport unit 113 of the heating section 104 can then receive the transport carriers 108 with the items 101 via the first divider 111a. The rollers 122 in the transport unit 113 then conveys the individual transport carriers 108 to the optional holding section 105 along a direction (illustrated by arrow 127). As the items 101 in the immersion fluid 110 move past the microwave windows 125, the microwave sources 116 apply microwave energy to both sides of the items 101 to raise an interior temperature of the items 101 to the target heating temperature. Subsequently, the rollers 122 in the transport unit 113 can convey the heated items 101 in the transport carriers 108 to the optional holding section 105.

The optional holding section 105 can receive the items 101 heated to the target heating temperature from the heating section 104 and generally maintain the items 101 at that temperature for a period of time (e.g., 10 minutes). As discussed above, by maintaining the items 101 at or near the target heating temperature can reduce or remove microbiological organisms in the items 101. At the end of the period of time, the optional holding section 105 conveys the transport carriers 108 with the items 101 to the cooling section 106. The cooling section 106 then applies the immersion fluid 110 from the cooling fluid supply 136 at a cooling temperature (e.g., 15° C.) to reduce an overall or interior temperature of the items 101 to room temperature or other suitable temperatures. The cooled items 101 can then be unloaded from the cooling section 106 to be further processed and/or stored.

Several embodiments of the processing system 100 can be used to efficiently sterilize or pasteurize items 101 without or with reduced negative effects on the items 101 than conventional techniques. In addition to techniques in which items 101 are heated by heating the products with hot air, hot water, or steam, items 101 are preferably heated by microwave. As a result, interior temperatures of the items 101 can be more efficiently raised than conventional heating techniques.

Several embodiments of the processing system 100 can also be used to efficiently sterilize or pasteurize items 101 without requiring pressurization of the sections in the processing system 100. Instead, at least some sections of the processing system 100 may be open to atmosphere. As discussed above, the items 101, such as packaged food products, typically include a certain amount of water content. Thus, the applied microwave energy in the heating section 104 may generate steam that cause explosion or rupture of the packaged food products. In some other processing systems, the sections are pressurized, for example, with an inert gas or air to prevent such steam explosion. However, such pressurization requires the sections be designed as pressure vessels, and thus increasing the costs of manufacturing and installation as well as operating complexity. In contrast, several embodiments of the processing system 100 utilizes the a hydrostatic pressure of the immersing fluid 110 on the items 101 to prevent or at least reduce the risk of steam explosion during heating, and thus avoid the need to pressurize the sections. The immersion fluid 110 can also help to homogenize temperatures of the items during preheating, heating, and/or cooling.

Figure 2:
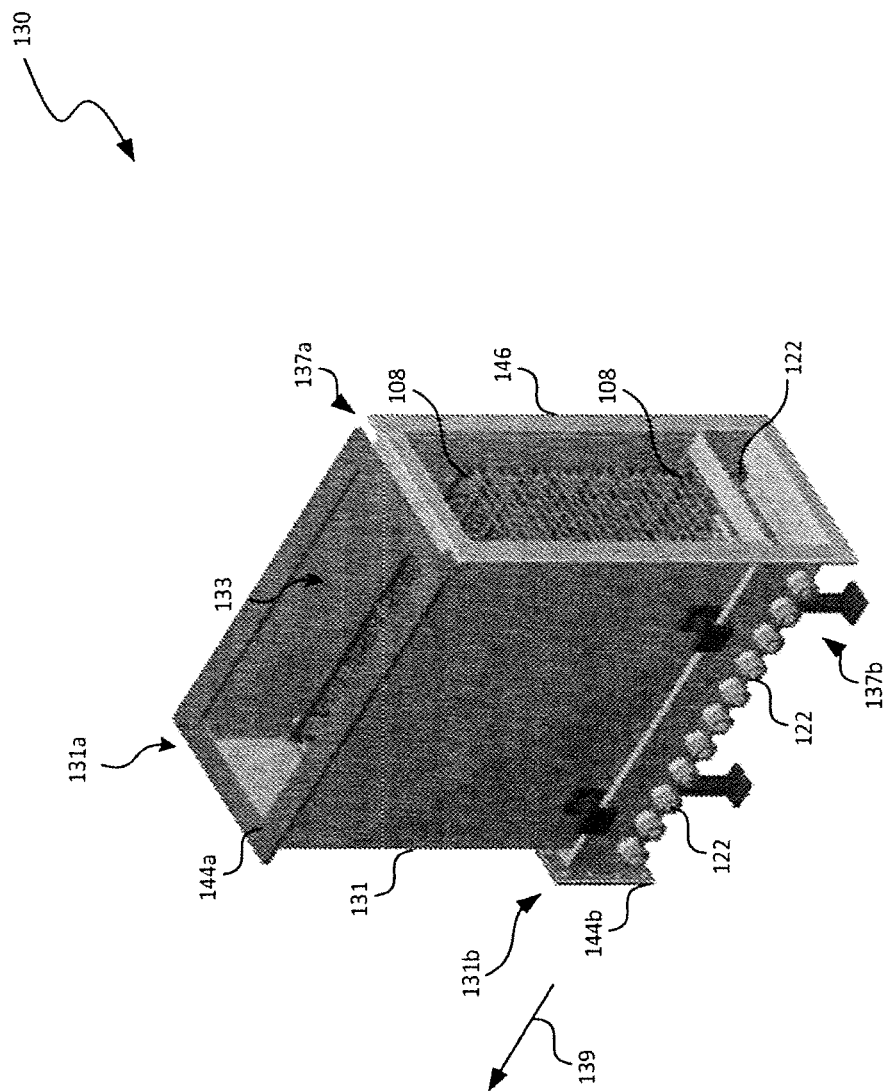
FIG. 2 is a perspective diagram illustrating a carrier assembly suitable for the processing system of FIG. 1 in accordance with embodiments of the disclosed technology.

FIG. 2 is a perspective diagram illustrating an example carrier assembly 130 suitable for the preheating section 102 or the cooling section 106 of the processing system 100 of FIG. 1 in accordance with embodiments of the disclosed technology. As shown in FIG. 2, the carrier assembly 130 can include a housing 131 having an inlet 131a with an inlet flange 144a and an outlet 131b with an outlet flange 144b. A back panel of the housing 131 is removed to show the transport carriers 108 for illustration purposes. In the illustrated embodiment, the housing 131 has a generally rectangular cross section between a first end 137a and a second end 137b. The inlet flange 144a and the outlet flange 144b are generally perpendicular to each other. In other embodiments, the carrier assembly 130 can have a trapezoidal, cylindrical, and/or other suitable cross sections sized and shaped to receive a plurality of transport carriers 108. In further embodiments, the carrier assembly 130 can also include friction fittings and/or other suitable couplers in addition to or in lieu of the inlet and/or outlet flanges 144a and 144b.

In the illustrated embodiment in FIG. 2, the carrier assembly 130 can include a plurality of rollers 122 proximate the second end 137b of the housing 131. The rollers 122 are configured to carry the bottom-most transport carrier 108 to exit the housing 131 via the outlet 131b, as indicated by an arrow 139. In one embodiment, the rollers 122 can be friction rollers. In other embodiments, the rollers 122 can include other suitable types of rollers. In further embodiments, the carrier assembly 130 can also include additional and/or different conveying components. For example, in certain embodiments, the carrier assembly 130 can also include a pneumatic push rods (not shown) proximate to the second end 137b of the housing 131 to carry the bottom-most transport carrier 108 to exit the housing 131 via the outlet 131b.

Though not shown in FIG. 2, the carrier assembly 130 can include a fluid inlet (e.g., a fluid distributer) and a fluid outlet (e.g., a nozzle) on the housing 131 to allow the immersion fluid 110 (FIG. 1) from the preheating fluid supply 132 (FIG. 1) or the cooling fluid supply 136 (FIG. 1) to circulate in an interior region 133 of the housing 131. The housing 131 can also include baffles, diverters, and/or other suitable flow modifying components configured to allow generally even flow of the immersion fluid 110 in the housing 131.

In operation, the carrier assembly 130 can receive a plurality of transport carriers 108 in a stack or other forms via the inlet 131a. The rollers 122 carries the bottom-most transport carrier 108 along the direction 139 to exit the outlet 131b. As the bottom-most transport carrier 108 exits the outlet 131b, another transport carrier 108 moves downward toward the second end 137b of the housing 131 to be carried through the outlet 131b. The process continues until no more transport carriers 108 are left in the housing 131.

Figure 3:
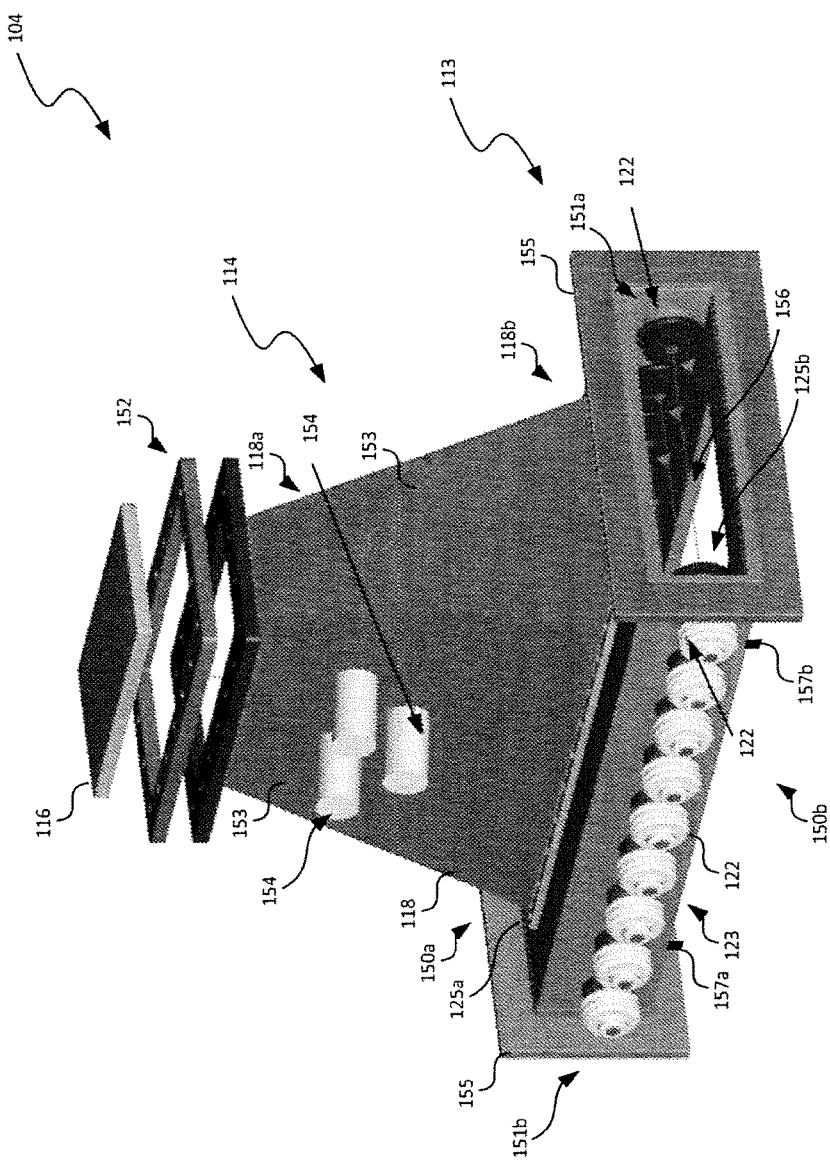
FIG. 3 is a perspective diagram illustrating a partial heating section suitable for the processing system of FIG. 1 in accordance with embodiments of the disclosed technology.

FIG. 3 is a perspective diagram illustrating an example heating section 104 suitable for the processing system 100 of FIG. 1 in accordance with embodiments of the disclosed technology in accordance with embodiments of the disclosed technology. As shown in FIG. 3, the heating section 104 can include a microwave assembly 114 coupled to a transport unit 113. Even though only one microwave assembly is shown for clarity in FIG. 3, the heating section 104 can include an additional microwave assemblies 114 (FIG. 1) coupled to the transport unit 113. In other embodiments, the heating section 104 may include multiple additional microwave assemblies (not shown) in any suitable arrangements.

As shown in FIG. 3, the microwave assembly 114 can include a microwave source 116 coupled to a first end 118a of a microwave guide 118 via a set of flanges 152. As discussed above with reference to FIG. 1, the microwave source 116 can include a single-mode or other suitable types of a microwave generator. In the illustrated embodiment, a second end 118b of the microwave guide 118 is coupled to the microwave window 125a of the transport unit 113. The microwave guide 118 also includes four sidewalls 153 extending between the first end 118a and the second end 118b. Each of the sidewalls 153 has a generally trapezoidal shape. In other embodiments, the microwave guide 118 can also include other suitable structures with suitable shapes and sizes.

In the illustrated embodiment, the microwave assembly 118 also includes one or more microwave tuners 154 carried by one or more sidewalls 153 of the microwave guide 118. The microwave tuners 154 can be configured to adjust a load of microwave energy delivered from the microwave source 116 to the items 101 (FIG. 1) via the microwave window 125a. The microwave tuners 154 can include one or more mechanical slide-screw tuners, manual impedance tuners, automated impedance tuners, or other suitable types of microwave tuners. In other embodiments, the microwave tuners 154 may have other suitable placements on the microwave assembly 114 and/or the transport unit 113. In further embodiments, the microwave tuners 154 may be eliminated.

As shown in FIG. 3, the transport unit 113 includes a transport housing 123 with a plurality of rollers 122. In the illustrated embodiment, the transport housing 123 has a generally rectilinear shape with flanges 155 at a first end 151a and a second end 151b. The transport housing 123 has a microwave window 125a at a first side 150a and another microwave window 125b at the opposite second side 150b. In one embodiment, the first and second windows 125a and 125b may be generally aligned with each other. In other embodiments, the first and second windows 125a and 125b may be offset from each other or have other suitable arrangements. The rollers 122 are positioned side by side and proximate the second side 150b and thus forming a channel 156 through while the transport carriers 108 (FIG. 1) may be carried by the rollers 122 from the first end 151a to the second end 151b. In other embodiments, the transport unit 123 can also have other suitable structures, shapes, and sizes suitable to deliver microwave energy to the items 101 (FIG. 1) carried on the transport carriers 108.

As shown in FIG. 3, the transport unit 113 can include a fluid inlet 157a (e.g., a fluid distributer) and a fluid outlet 157b (e.g., a nozzle) on the transport housing 123 to allow the immersion fluid 110 (FIG. 1) from the tempered fluid supply 134 (FIG. 1) to circulate in the channel 156 of the transport housing 123. The transport housing 123 can also include baffles, diverters, and/or other suitable flow modifying components configured to allow generally even flow of the immersion fluid in the transport housing 123.

In operation, individual transport carriers 108 carrying items 101 are received at the first end 151a of the transport housing 123 while the immersion fluid 110 from the tempered fluid supply 134 fills and circulates in the channel 156. The rollers 122 can then carry the individual transport carriers 108 from the first end 151a to the second end 151b. The items 101 can then receive microwave energy from the microwave source 116 while immersed in the immersion fluid 110 when the items 101 pass under/above the microwave windows 125a and 125b.

In one embodiment, when a transport carrier 108 is generally aligned with the microwave windows 125a and 125b, the rollers 122 may be stopped. The microwave source 116 may then be turned on to deliver microwave energy to the items 101 on the transport carrier 108 for a period of time (e.g., about 10 seconds to about 3 minutes). Subsequently, the rollers 122 are turned on to carry the transport carrier 108 toward the second end 151b. In another embodiment, the rollers 122 may be slowed but not stopped when the transport carrier 108 is at least partially exposed through the microwave windows 125a and 126b while the microwave source 116 is turned on to deliver microwave energy through the microwave windows 125a and 125b. In a further embodiment, the rollers 122 may carry the transport carriers 108 through the channel 156 at a constant speed. In yet further embodiments, the rollers 122 may carry the transport carriers 108 through the channel 156 in other suitable manners.

Figure 4:
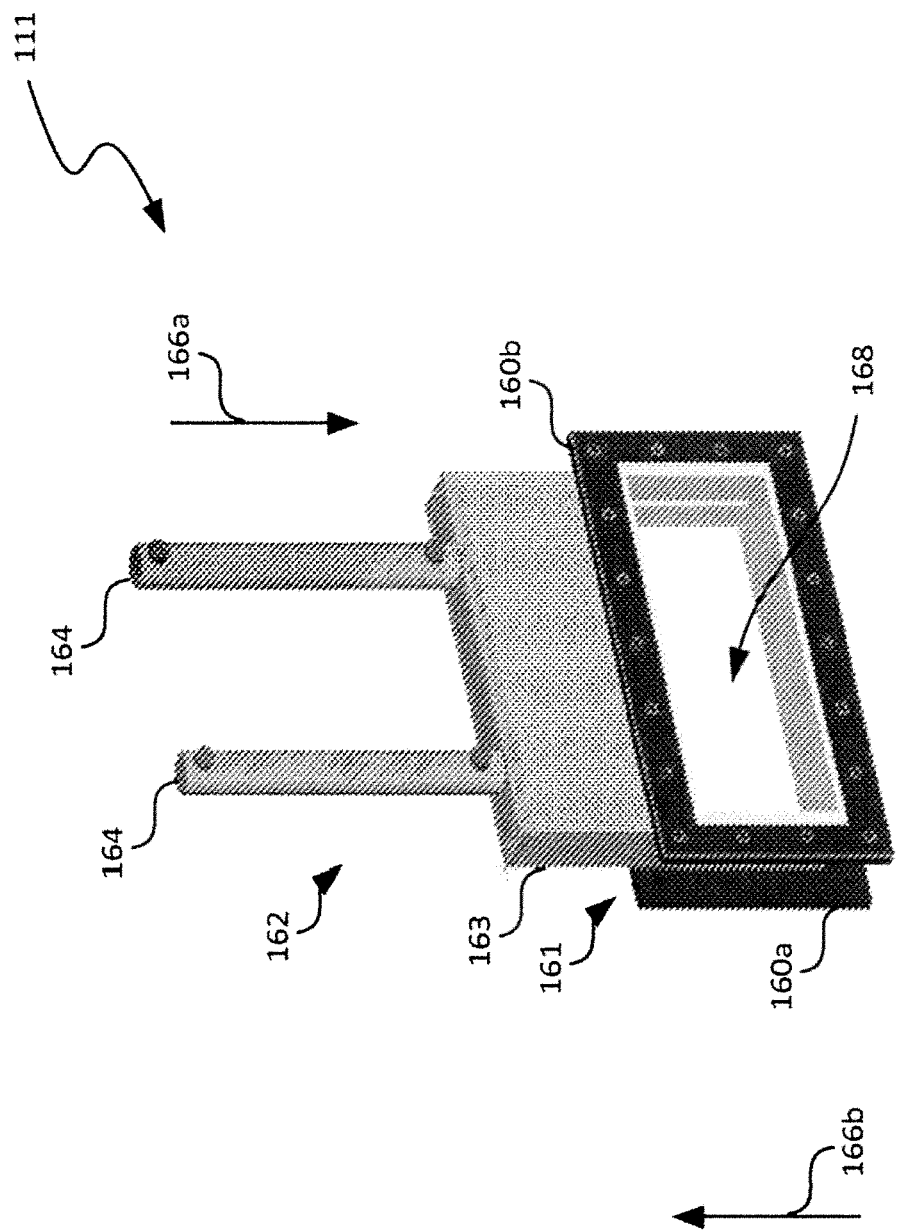
FIG. 4 is a perspective diagram illustrating an example divider suitable for the processing system of FIG. 1 in accordance with embodiments of the disclosed technology.

FIG. 4 is a perspective diagram illustrating an example divider 111 suitable for the processing system 100 of FIG. 1 in accordance with embodiments of the disclosed technology. As shown in FIG. 4, the divider 111 can include a pair of flanges 160a and 160b spaced apart from each other by a divider channel 161 and a gate 162 positioned in the divider channel 161. In the illustrated embodiment, the gate 162 includes a blocking member 163 attached to one or more lifting members 164 (two are shown for illustration purposes). The blocking member 163 can include a plate, slab, sheet, or other suitable structures constructed from a metal, alloy, plastic, rubber, or any other suitable materials with sufficient rigidity. In one embodiment, the lifting members 164 may be formed integral with the blocking member 163. In other embodiments, the lifting members 164 may be attached to the blocking member 163 with one or more fasteners, glue, or other suitable attachment mechanisms (not shown). Though not shown in FIG. 4, the divider 111 can also include seals, rails travel guides, and/or other suitable components attached on and/or formed in the flanges 160a and 160b and/or the gate 162.

In one mode of operation, the lifting members 164 may be actuated by an electrical motor, a pneumatic cylinder, and/or other suitable driving mechanisms (not shown) to push the blocking member 163 into the divider channel 161 between the flanges 160a and 160b, as indicated by arrow 166a. The blocking member 163 can thus at least partially isolate the immersion fluid 110 (FIG. 1) on either side of the flange 160a or 160b. In another mode of operation, the lifting members 164 may also be actuated to remove the blocking member 163 from the divider channel 161, as indicated by arrow 166b. As shown in FIG. 4, once the blocking member 163 is at least partially removed, a passage 168 forms through the flanges 160a and 160b allowing transport carriers 108 (FIG. 1) to pass through.

Figure 5A:
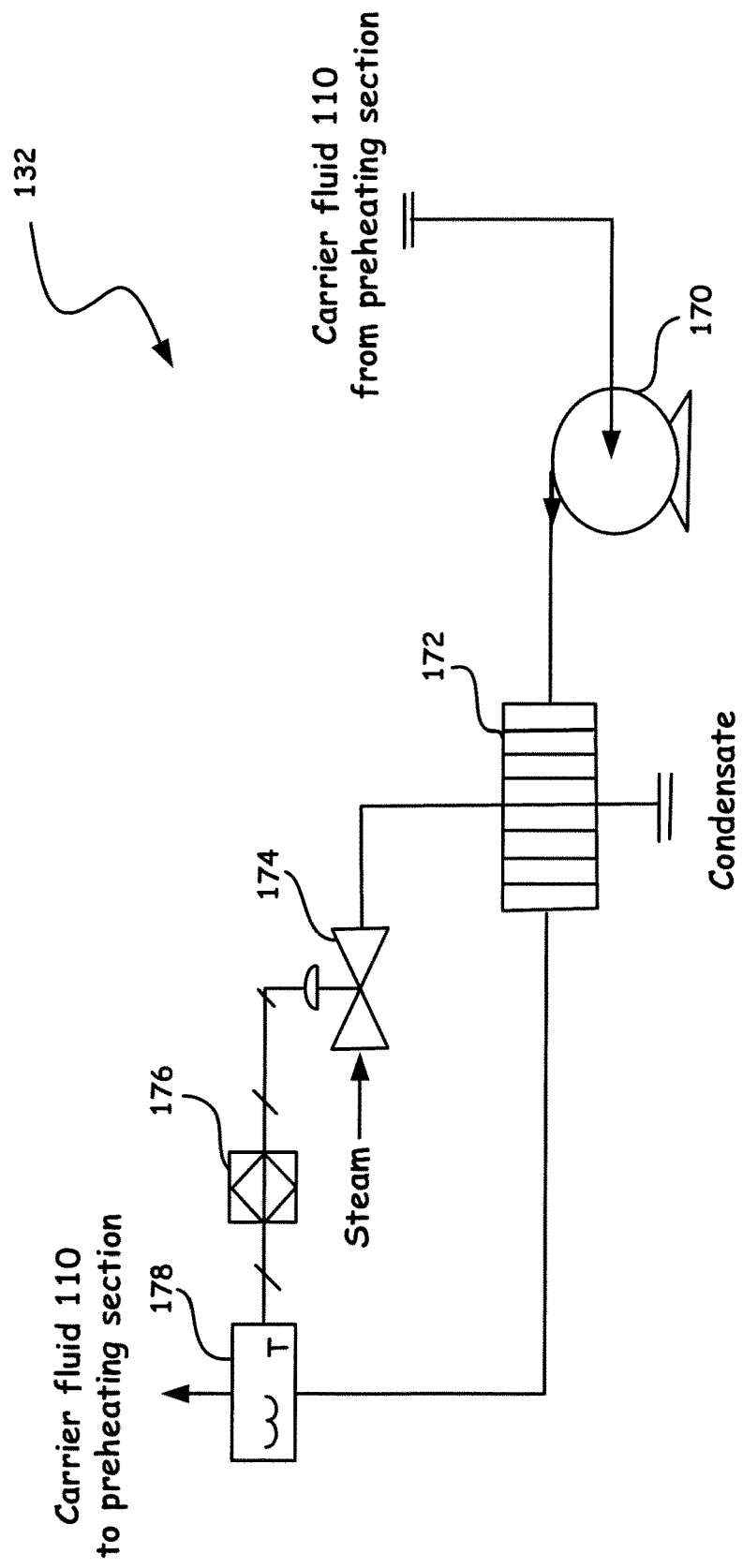
FIG. 5A is a schematic diagram of the preheating section of the processing system of FIG. 1, in accordance with embodiments of the disclosed technology.
Figure 5B:
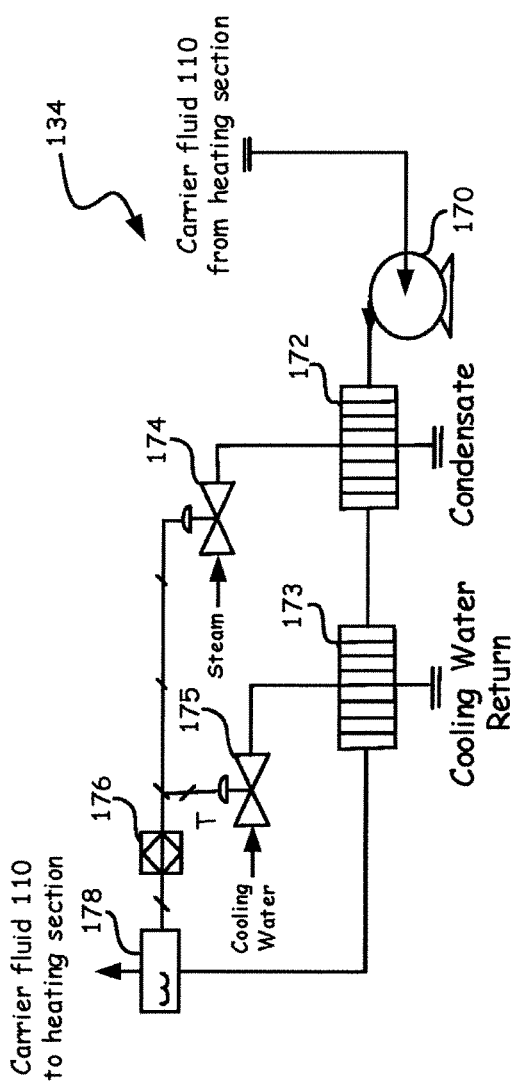
FIG. 5B is a schematic diagram of the heating section of the processing system of FIG. 1, in accordance with embodiments of the disclosed technology.
Figure 5C:
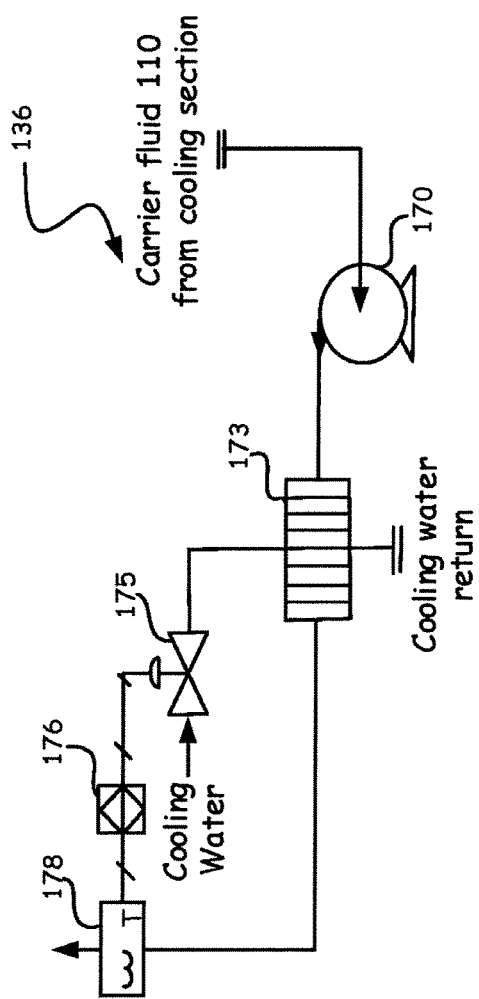
FIG. 5C is a schematic diagram of the cooling section of the processing system of FIG. 1, in accordance with embodiments of the disclosed technology.

FIGS. 5A-5C are schematic diagrams of preheating, tempered, and cooling fluid supplies 132, 134, and 136 suitable for the preheating section 102, heating section 104, and cooling section 106 of the processing system 100 of FIG. 1, respectively, in accordance with embodiments of the disclosed technology. In FIGS. 5A-5C, identical reference numbers identify elements similar in structure and/or function. Even though particular components are shown in FIGS. 5A-5C, the fluid supplies 132, 134, and 136 may also include a flow meter, pressure gauge, pressure transmitter, valve position switches/transmitters, and/or other suitable components (not shown).

As shown in FIG. 5A, the preheating fluid supply 132 can include a circulating pump 170, a steam heat exchanger 172, a steam valve 174, a temperature sensor 178, and a controller 176 operatively coupled to one another. The circulating pump 170 can include a centrifugal pump, a gear pump, or other suitable types of pump. The steam heat exchanger 172 can include a plate-and-tube, plate, or other suitable types of heat exchanging component. The temperature sensor 178 can include a thermocouple, a resistance temperature detector, or other suitable types of temperature sensor. The steam valve 174 can include an actuated globe valve, butterfly valve, ball valve, or other suitable types of valve. The controller 176 can include a single-loop controller or a control module of a programmable process controller.

In operation, the circulating pump 170 receives the immersion fluid 110 from the preheating section 102 (FIG. 1) and moves the received immersion fluid 110 to the steam heat exchanger 172. Steam (e.g., 60 Psig steam) is introduced through the steam valve 174 to heat the immersion fluid 110 while the immersion fluid 110 passes through the steam heat exchanger 172. The temperature sensor 178 measures the temperature of the immersion fluid 110 exiting the steam heat exchanger 172 and provides the measurement to the controller 176. The controller 176 can then adjust the steam valve 174 based on a set-point for the temperature of the immersion fluid 110 exiting the steam heat exchanger 172 and the measurements from the temperature sensor 178.

In the illustrated embodiment, the introduced steam is collected as condensate after passing through the heat exchanger 172. The collected condensate may then be recycled, drained, or otherwise processed. In other embodiments, the heat exchanger 172 may be substituted by a steam-water mixer (not shown) that is configured to directly mix the introduced steam with the immersion fluid 110.

As shown in FIG. 5B, the tempered fluid supply 134 can be generally similar to the preheating fluid supply 132 shown in FIG. 5A except having a cooling heat exchanger 173 in series with the steam heat exchanger 172 and a cooling water valve 175 configured to introduce cooling water to the cooling heat exchanger 173. Even though the cooling heat exchanger 173 is shown in FIG. 5B as downstream from the heat exchanger 172, in other embodiments, the cooling heat exchanger 173 can also be positioned upstream of the steam heat exchanger 172 or in other suitable places.

In operation, the controller 176 can adjust both the cooling water valve 175 and the steam valve 174 to achieve a set-point for the temperature of the immersion fluid 110 to the heating section 104 (FIG. 1). For example, the controller 176 may be configured to perform split control according to which positive control actions are directed to the steam valve 174 while negative control actions are directed to the cooling water valve 173. Thus, the immersion fluid 110 may be heated by steam when passing through the steam heat exchanger 172 and cooled by cooling water when passing through the cooling heat exchange 173. In other examples, the controller 176 may also be configured to perform step control, threshold control, or other suitable control schemes.

As shown in FIG. 5C, the cooling fluid supply 136 can be generally similar to the tempered fluid supply 134 of FIG. 5B except the cooling fluid supply 136 does not include the steam heat exchanger 172 or the steam valve 174. In operation, the cooling water valve 175 admits cooling water to the cooling heat exchanger 173 to remove heat from the immersion fluid 110. The temperature sensor 178 measures the temperature of the immersion fluid 110 exiting the cooling heat exchanger 173 and provides the measurements to the controller 176. The controller 176 can then adjust the cooling water valve 175 based on a set-point for the temperature of the immersion fluid 110 exiting the cooling heat exchanger 173 and the measurements from the temperature sensor 178.

Figure 6:
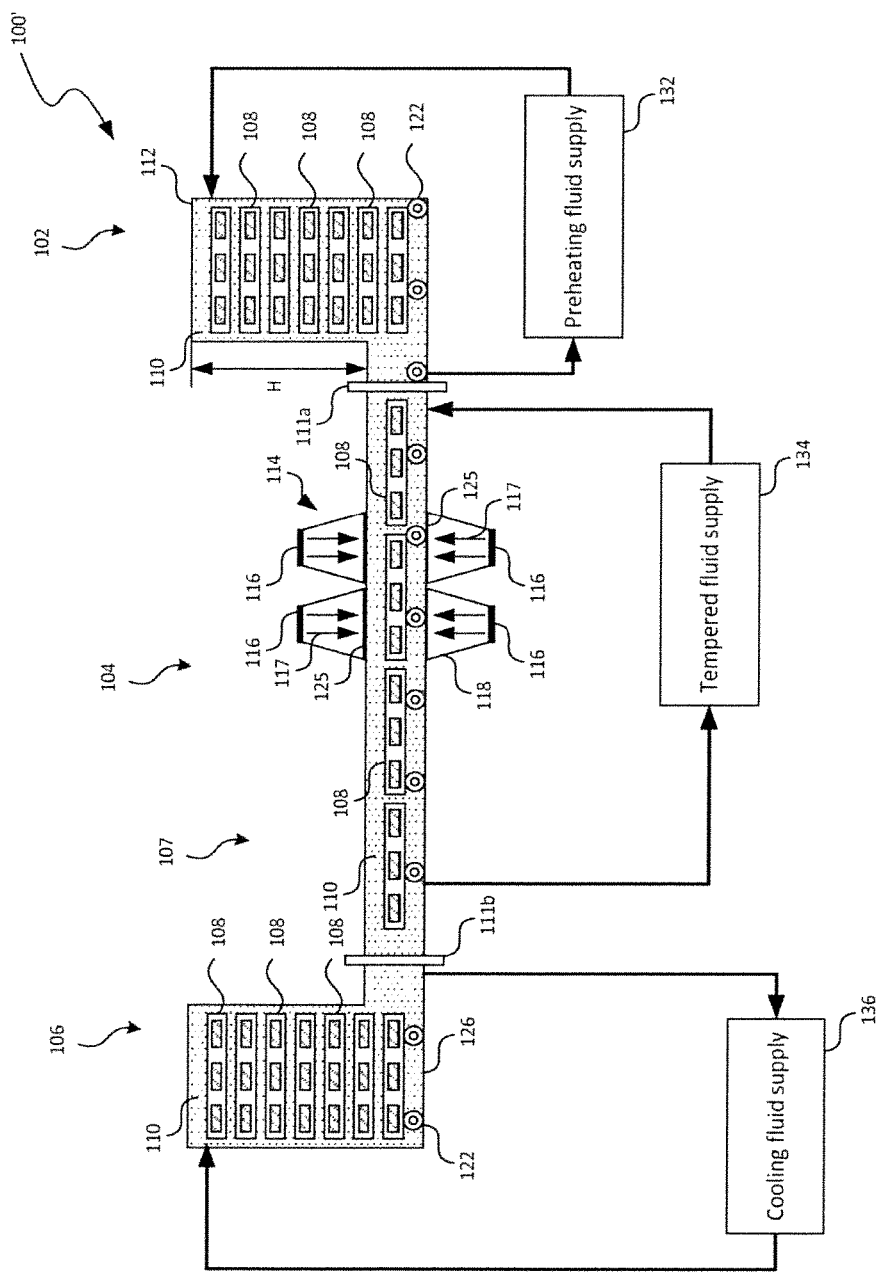
FIG. 6 is a schematic diagram illustrating another processing system useful for sterilization or pasteurization in accordance with embodiments of the disclosed technology.

FIG. 6 is a schematic diagram illustrating another processing system 100' useful for sterilization or pasteurization in accordance with embodiments of the disclosed technology. As shown in FIG. 6, the processing system 100' can be generally similar to that of FIG. 1 except that the preheating section 102 and the cooling section 106 can be at a generally similar elevation H with respect to the heating section 104. Also, the processing system 100' in FIG. 6 does not include the optional holding section 105. Instead, the processing system 100' includes a transport section 107 (e.g., similar mechanically to the transport unit 113 discussed above for FIG. 3) between the preheating section 102 and the cooling section 106. The transport section 107 can be at an elevation generally similar to that of the heating section 104. In other embodiments, the transport section 107 may be omitted, and the heating section 104 may be coupled directly to the cooling section 106. In further embodiments, the processing system 100' may include other suitable components, assemblies, and sections in suitable arrangements.

Figure 7A:
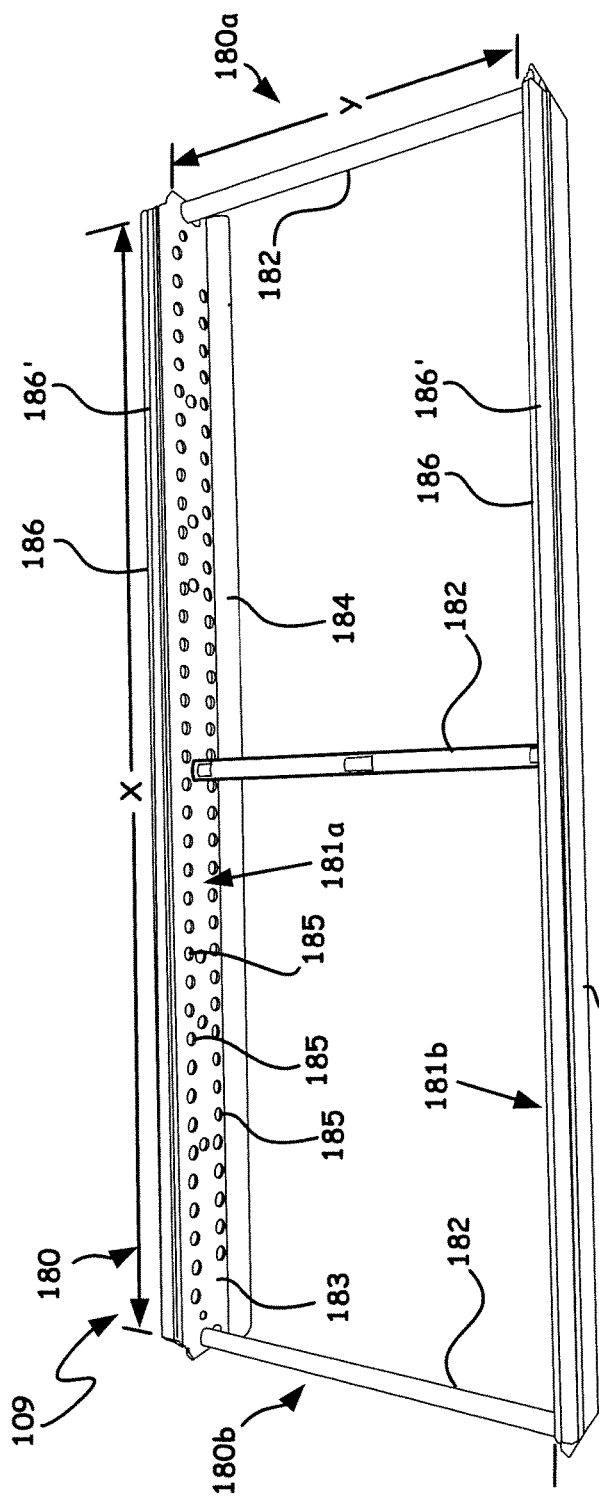
FIG. 7A is a perspective view of an example transport carrier framework.

FIG. 7A is a perspective view of an example "Universal" transport carrier framework 109, configured with often, but necessarily rectangular dimensions (denoted as x and y (inner dimension)) to be utilized by the processing system 100 of FIG. 1 or for the processing system 100' shown in FIG. 6. As shown in FIG. 7A, the transport carrier framework 109 can include a carrier base 180 having coupled (e.g., threadedly coupled) one or more cross members 182. The carrier base 180 is configured with a size and shape based on the system configuration parameters shown in, for example, FIG. 1, and at least one of a shape or size of the items 101 (FIG. 1) to be carried therein/thereon. For example, in the illustrated embodiment, the carrier base 180 has a generally rectilinear shape with a first side 181a and a second side 181b (collectively referred to as side or sides 181) extending between a first end 180a and a second end 180b of the base 180. In other embodiments, the carrier base 180 can have a generally oval, square, and/or other suitable shape.

FIG. 7A, in illustrating a beneficial non-limiting structure, shows the first and second sides 181a and 181b configured as a first side plate 183 and a second side plate 183'. Such side plates 181a and 181b are also shown configured with therethrough apertures 185 (3 denoted with arrows for simplicity) provided for each side 181a and 181b so as to not only operate as fluid channels to aid in item 101 fluid immersion within system 100, as shown in FIG. 1, but beneficially, such apertures 185 in number also reduce the overall weight of the carrier transport framework 109 and the corresponding assembled transport carrier 108, to be discussed below.

Figure 7B:
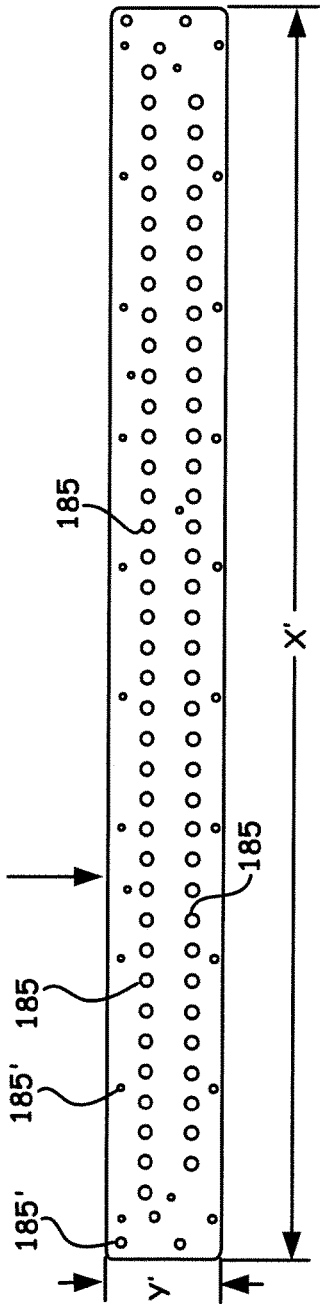
FIG. 7B shows a side view of an example side plate for the transport carrier framework.

FIG. 7B shows a side view of side plate 183' detailing an example embodiment of the therethrough apertures 185 to enable the reader to have a better perspective of the design features. Side plate 183', which can, and often does mirror in design, side plate 183, also is shown with additional apertures 185' of varying diameters or structure (e.g., through holes, threaded holes, slots, etc.), that can, for example, aid in coupling other components (e.g., cross members 182) to the overall framework of the transport carrier 108. The side plates 183, 183', can dimensionally also have any desired rectilinear length (x') and width (y'), depending on the design of the carrier transport framework 109. However, such sideplates 183, 183' are not limited to merely rectangular structures as shown by the example FIG. 7A and FIG. 7B embodiments but can be configured with dimensions differing (irregular shapes, oval shapes, etc.), from that shown so as to aid in weight design and system performance. However, to give an appreciation for the dimensionalities of a working non-limiting design, a length (x') can be up to about 31 inches or greater with a width (y') of up to about 3.0 inches or greater.

It is to be also noted that the first side plate 183 and the second side plate 183' are configured to be coupled to often a pair of supports, e.g., a first support 184 and a second support 186, as shown in FIG. 7A, to enable a robust structure for the transport carrier framework 109. While not necessary for all embodiments, the second supports 186, which extend transversely between the first end 180a and the second end 180b, are also shown having a grooved configuration 186' to receive and engage rollers 122, as discussed above, or other suitable components of the processing system 100, as shown in FIG. 1, for moving the overall carrier base 180.

It is also to be noted that the cross members 182 often are configured as an elongated component extending between the first and second sides 181a and 181b. The cross members 182 can have a generally circular, rectangular, cubic, oval, or any other suitable cross-sectional area. While only three cross members 182 are shown for illustration purposes in FIG. 7A, it is to be understood that two, four, or any suitable number of cross members 182 generally and substantially parallel to one another, can also be utilized at varying positions within the carrier base 180 without departing from the scope of the design. It is also to be appreciated that the components of the transport carrier framework 109 (e.g., plates 183, 183', cross members 182, and any other component utilized though not shown in FIG. 7A), may be constructed from materials such as a metal (e.g., aluminum), a metal alloy (e.g., stainless steel), plastics, invar, or other suitable materials with sufficient mechanical strength but that beneficially, as desired, also reduce microwave reflectivity so as to aid in proper uniform item 101 heating.

Figure 8A:
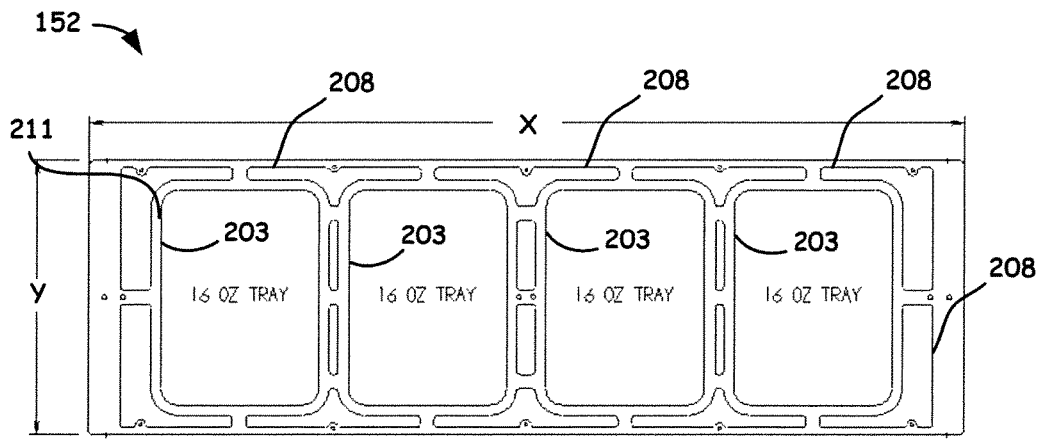
FIG. 8A shows a top down view of an example tray design configured to receive 16 ounce food items
Figure 8B:
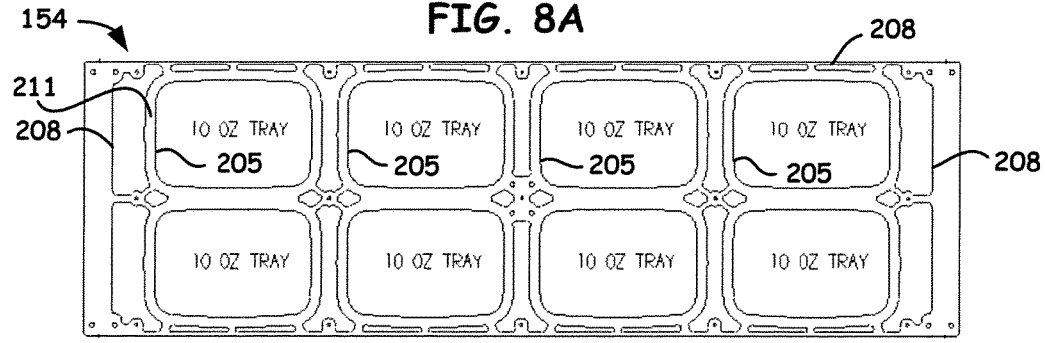
FIG. 8B illustrates a top down view of an example tray design configured for receiving a plurality of 10 ounce food items.
Figure 8C:
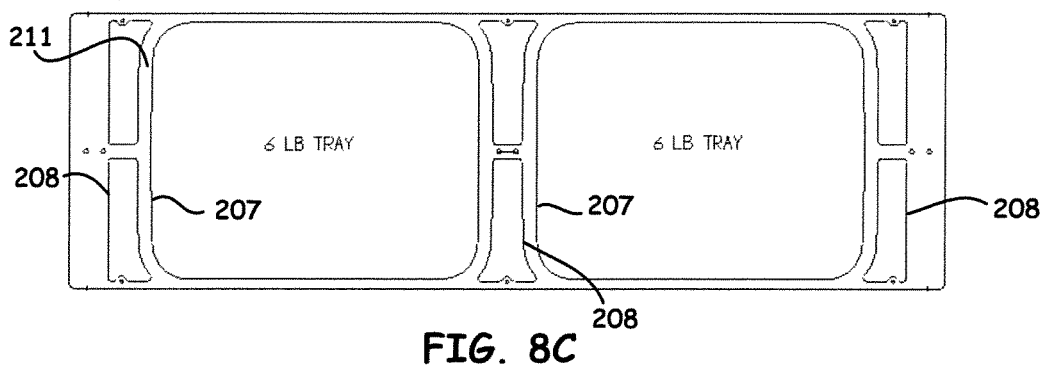
FIG. 8C illustrates a top down view of an example tray design configured for receiving a plurality of 6 pound food items.

FIG. 8A, FIG. 8B, and FIG. 8C illustrate top down views of an important aspect of the embodiments herein. Specifically, such figures show by example, trays, containers, receptacles, etc., (hereinafter referred to as trays) that are configured to receive one but often a plurality of desired items 101 when incorporated in a transport carrier framework 109, as shown and discussed above for FIG. 7A. The end result is a novel assembly for the transport carrier 108 discussed below in detail and as briefly touched upon above.

In particular, FIG. 8A shows an example tray (denoted by the reference numeral 152) configured to be coupled to the transport carrier framework 109 (FIG. 7A) and also beneficially configured to contain disposed products, e.g., 16 ounce food packages in a user friendly manner. FIG. 8B shows an example tray (denoted by the reference numeral 154) configured to be also coupled to the transport carrier framework 109 (FIG. 7A) (removable in an easy manner and exchanged with any of the trays discussed herein) and also beneficially configured to contain disposed, e.g., 10 ounce food packages, in a user friendly manner, while FIG. 8C shows an example tray (denoted by the reference numeral 156) configured to be also interchangeably coupled to the transport carrier framework 109 (FIG. 7A) (removable in an easy manner and exchanged with any of the trays discussed herein) and also beneficially configured to contain disposed, e.g., 6 lb. food packages, in a user friendly manner.

In particular with respect to FIG. 8A, FIG. 8B, and FIG. 8C, the respective trays 152, 154, and 156 are often, but not necessarily, configured as a plate having beneficial features. To explain, each tray 152, 154, and 156 illustrated in FIG. 8A, FIG. 8B, and FIG. 8C, show configured apertures 203, 205, 207 respectively (reference lines point to the wall of the apertures) configured to contain and substantially secure desired items 101 (FIG. 1) (e.g. a 16 ounce food package (FIG. 8C)). In operation, items 101 (FIG. 1) are coupled in a secured manner to an aperture (203, 205, 207) based on the design of the packages in combination with the design of a respective tray 152, 154, and 156. As a beneficial aspect, the items 101 often have a shaped construction such as, for example, a lip a flange portion, or other packaging construction that can mate with the upper surface 211 of the trays 152, 154, and 156 with a bulk portion that extends downwardly a designed distance below the bottom surface (not denoted) so as to be positioned and substantially secured by the apertures 203, 205, 207 of the trays 152, 154, and 156.

It is also to be appreciated that the apertures 203, 205, 207, as shown in FIG. 8A, FIG. 8B, and FIG. 8C, are configured to segregate the items 101 to aid in individual uniform heating of the items 101 because of the overall design of the system (FIG. 1). FIG. 8A, FIG. 8B, and FIG. 8C also show ancillary apertures 208 for each tray 152, 154, and 156. Such ancillary apertures 208, much like the apertures 185 for the plate shown in FIG. 7A and FIG. 7B, are specifically incorporated by size, shape and number to not only operate as fluid channels for the immersion fluid 110 to aid in enveloping the items 101 with such fluid, but also and beneficially, to further reduce the overall weight of the carrier transport framework 109 and the corresponding assembled transport carrier 108.

Moreover, the trays, e.g., 152, 154, and 156, taking the example of being configured as plates, are often constructed of a material (in addition to similar materials of the transport carrier 108) and with structural features along with the transport carrier 108 so as to influence the heating profile of the individual items 101 (FIG. 1). With respect to the materials themselves, the plates 152, 154, and 156, as shown in FIG. 8A, FIG. 8B, and FIG. 8C in combination with the materials utilized in construction of the coupled transport carrier framework 109 (FIG. 7A), are to be appreciated as often being substantially constructed from a metal (e.g., aluminum, titanium, magnesium) and/or a metal alloy (e.g., various aluminum, magnesium, and stainless steel alloys known in the art), preferably of at least up to about 80% metal or up to about 80% metal alloy, for a resultant transport carrier 108 assembly.

With respect to structural aspects, the construction of the cross members 182 and any other included component, are adjusted, for example, relative to the first and second sides 181a and 181b and/or the first end 180a and the second end 180b. Surprisingly, and unexpectedly, because of the substantial metal and/or metal alloy construction of the trays (e.g., 152) when coupled to the food transport carrier 109 (FIG. 7A) as immersed in water, the reflected microwave energy when irradiating food products (e.g., items 101), drops by up to about 50% (thus more absorbed energy) for a single-mode microwave heating cavity, as disclosed herein, when compared to for example, other previous designs by the applicants utilized to hold the items 101 disclosed herein.

FIG. 9A and FIG. 9B show different top perspective views of example trays used herein so as to give the reader an appreciation of other beneficial design features. In particular, FIG. 9A now shows an 8 ounce tray 158, capable of holding a plurality of items 101, while FIG. 9B shows a 10 ounce tray 154 design, as also illustrated in FIG. 8A. In these example tray 158, 154 depictions, the trays show in more detail the apertures 201, 203, for different trays 158, 154. As discussed above, the items 101 (FIG. 1) often have a lip (flange portion) that mates with the upper surface 211 of the trays 152, 154, and 156 with a bulk portion that extends downwardly a designed known distance below the bottom surface (not denoted) of the trays themselves. In FIG. 9A and in FIG. 9B, the example embodiments also illustrate a non-limiting method of securing the items 101 (FIG. 1) once positioned. In particular, the figures now include using, for example, clips 213 (not all denoted for simplicity) or other means known in the art (tie-wraps, etc.) to otherwise secure the items 101 to an individual tray e.g., tray 154.

FIG. 10A and FIG. 10B illustrate top perspective views of two assembled transport carriers 108 that incorporate the removable and interchangeable tray 152, 156 configurations (as shown in FIG. 8A and FIG. 8C) as part of the overall assembly. In particular, FIG. 10A shows a 16 ounce tray 152 having item apertures 203 and ancillary apertures (e.g., 208 one denoted for simplicity) being utilized as an aspect of transport carrier 108 while FIG. 10B shows a 6 lb. item tray 156 having designed item apertures 207 and ancillary apertures 208 being incorporated. Mounting of the plates (e.g., trays 152, 156) can routinely be accomplished via, for example, mounting such plates 152, 156 on configured cross members 182, as shown in FIG. 7A within the boundaries of the first side plate 183 and the second side plate 183' and coupling the plates 152, 156 to such cross members 182 (FIG. 7A) using any known coupling technique known in the art, e.g., using bands, straps, tie-wraps, clips, hooks, springs, simple adhesives, etc. An example coupling embodiment is shown in FIG. 10A wherein one or more designed mounting holes 257 in the plate (e.g., 152) can be used for insertion of a tie-wrap or other means so as to couple to a configured cross member 182 (as detailed in FIG. 7A). FIG. 10B has a plate 156 construction wherein a pair of ancillary apertures 208 enable coupling arrangements to a cross member 182 if so desired. As another example embodiment, the side plates, 183, 183', as shown in FIG. 7A and as shown in FIG. 10A and FIG. 10B, can have configured pins or lips (flanges) (not shown), etc., designed into the structures so as to have a base that not only secures the plates, e.g., 152, 156, but also enables easy mounting.

Figure 11:
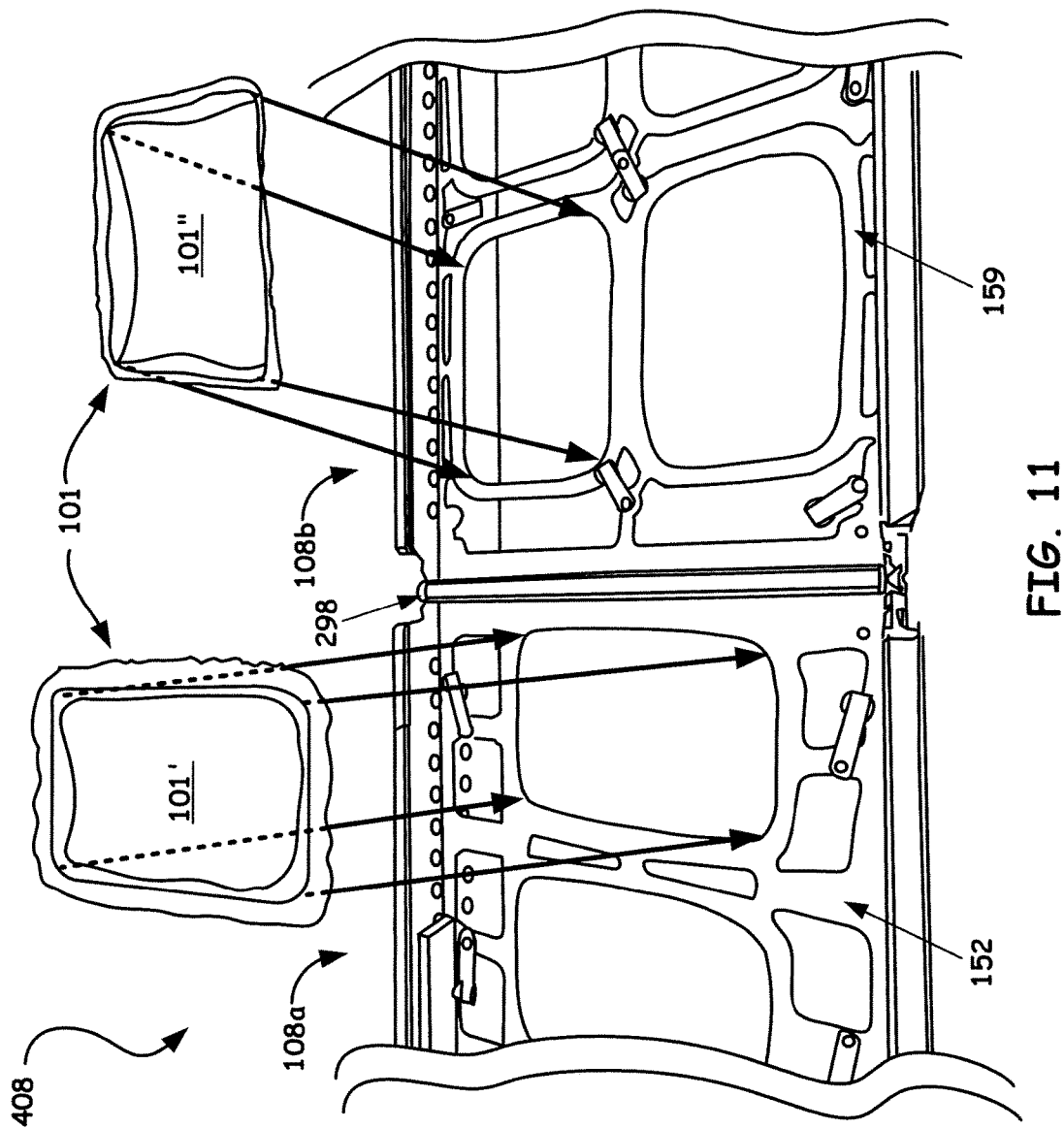
FIG. 11 shows a top perspective view of a longitudinal item transport carrier assembly.

FIG. 11 shows a top perspective cut-away view of a longitudinal item (e.g., 101', 101") transport carrier 408 assembly configured to provide a plurality (two shown for simplicity) of transport carriers 108a and 108b along a column. As only two carriers are shown for simplicity, transport carriers 108a and 108b are nonetheless shown coupled together by connectors 298 (shown by example as a rod) known in the art and numbering (N) in an amount (e.g., N−1) depending on the number of overall coupled carriers. Accordingly, longitudinal item transport carrier 408 assembly and correspondingly the processing systems herein (e.g., 100 as shown in FIG. 1) can be configured to carry and process two, three, or any suitable number of columns of items 101 (FIG. 1), in a respective tray 152, 159 that each can be configured with the same but more often different aperture configurations so as to receive different item packing shapes and sizes.

Example connectors 298 together or alone can include but are not limited to: welded connections, rods, captive fasteners, anchors, bands, straps, clamps, tensioners, bolts, screws, bushings, cotter pins, wire clips, dowel pins, industrial pins, fixturing pins, lockbolts, locknuts, nails, nuts, screws, springs, spacers, washers, rivets, rings, and threaded components. Thus, as shown in FIG. 11, different trays 152, 159, configured for different sizes and shapes, are utilized for receiving respectively shaped one or more packaged items 101', 101" (arrows denoting shapes and sizes directed to a respective tray 152, 159 for positioning). Accordingly, similar to the discussion above for a single transport carrier 108, longitudinal item (e.g., 101', 101") transport carrier 408 assembly for example, may be carried by the rollers 122 (FIG. 1) or any transport means (e.g., a transport mechanism attached to the sides 183, 183' (FIG. 7A), as received from the preheating section 102, and thereafter may be directed from the first end 151a to the second end 151b (FIG. 3) of the transport unit 113 (FIG. 3), wherein microwave energy can be directed to the items 101', 101". For example, such a transport mechanism attached to the sides can include a roller or belt on one or both sides of the metal frame. As similarly discussed above, in this example configuration, the longitudinal item (e.g., 101', 101") transport carrier 408 assembly carrying sterilized or pasteurized one or more packaged items 101', 101" can then be further directed to the optional holding section 105 and/or cooling section 106 (FIG. 1) as desired.

Figure 12:
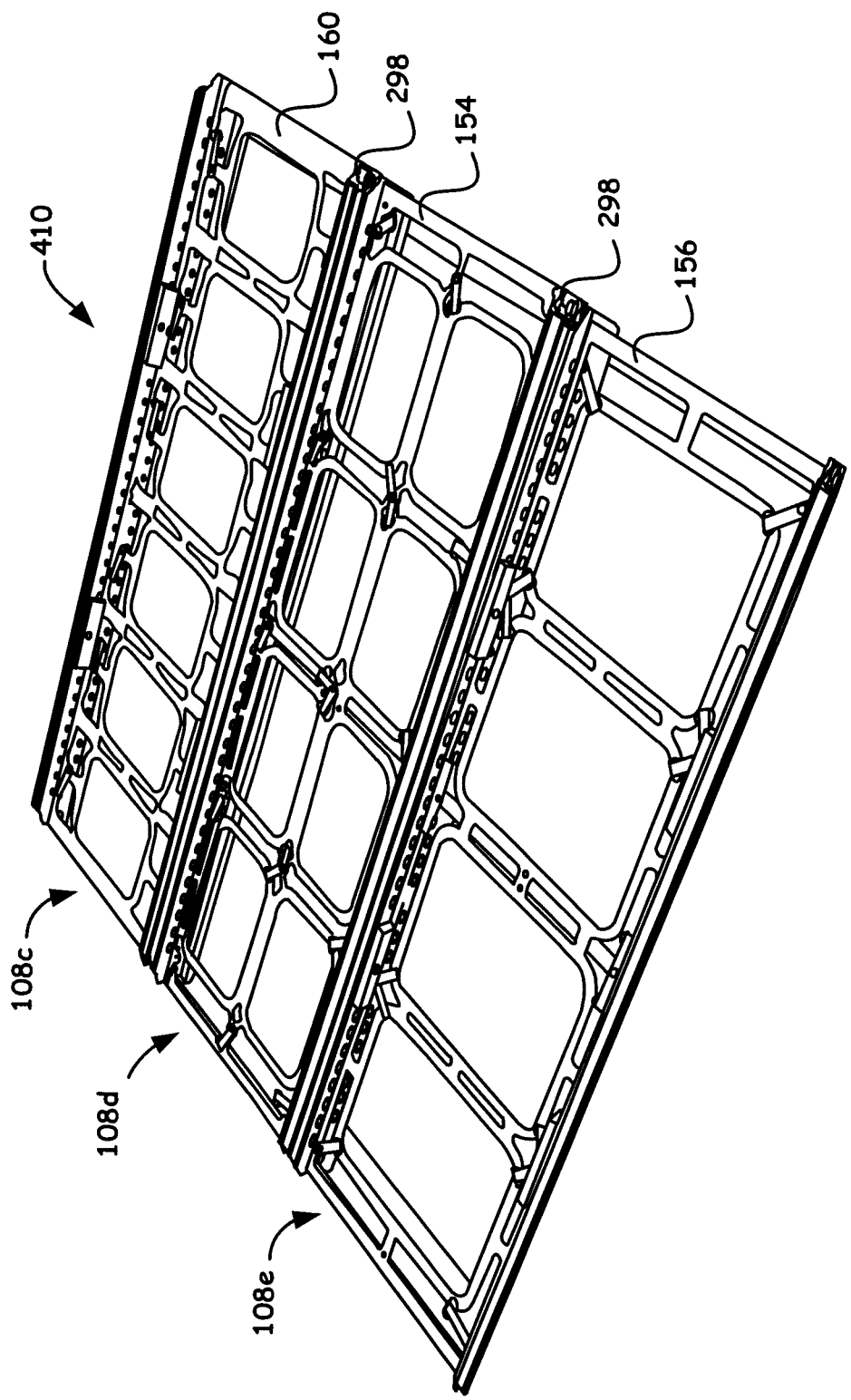
FIG. 12 shows a top perspective view of a parallel item transport carrier.

FIG. 12 shows a top perspective view of a parallel item transport carrier 410 assembly configured to provide a plurality (e.g., three) of transport carriers 108c, 108d, and 108e along a row. In particular, FIG. 12 shows a parallel item transport carrier 410 which can correspondingly be incorporated into the processing systems herein (e.g., 100 as shown in FIG. 1) to carry and process two, three, or any suitable number of rows of items 101 (FIG. 1), in a respective tray, e.g., 160, 154 (10 ounce tray items), and 156 (6 pound tray items), that each can be configured with the same but more often different apertures configurations so as to receive different item packing shapes and sizes.

It is also to be appreciated that similar to the example transport carrier 408 assembly embodiment of FIG. 11, each individual transport carrier 108c, 108d, and 108e is also shown coupled together by connectors 298, known in the art and of a material that can be metallic, polymeric, or constructed with other suitable materials with desired mechanical properties. Example connectors 298 for FIG. 12 also together or alone can include but are not limited to: welded connections, rods, captive fasteners, anchors, bands, straps, clamps, tensioners, bolts, screws, bushings, cotter pins, wire clips, dowel pins, industrial pins, fixturing pins, lockbolts, locknuts, nails, nuts, screws, springs, spacers, washers, rivets, rings, and threaded components.

Thus, as shown in FIG. 12, different trays 160, 154, 156, configured for different shaped sizes and shapes, are utilized for receiving respectively shaped one or more packaged items (e.g. see 101', 101" in FIG. 11). It is to be noted that the process system shown in FIG. 1 can be reconfigured to include three, four, or any desired number of parallel sets of microwave assemblies to process parallel item transport carrier 410 assembly having two, three, or any suitable number of transport carriers, e.g., 108c, 108d, and 108e.

Based on such a configuration and similar to the discussion above for a single transport carrier 108, the parallel item transport carrier 410 assembly may be carried by the rollers 122 (FIG. 1) as received from the preheating section 102, and thereafter may be directed from the first end 151a to the second end 151*b* (FIG. 3) of the transport unit 113 (FIG. 3), wherein microwave energy can be directed to deliver microwave energy to the items (101 of FIG. 1) simultaneously via corresponding microwave windows 125 (FIG. 1) in the transport housing 123. As similarly discussed above, in this example configuration, the parallel item transport carrier 410 assembly carrying sterilized or pasteurized one or more packaged items can then be further directed to the optional holding section 105 and/or cooling section 106 (FIG. 1) as desired.

It is also to be noted that transport mechanisms, in addition to rollers 122, can include a chain driven mechanism (not shown), or a conveyor belt assembly (not shown) and one or more guide rails as disclosed in the incorporated by reference U.S. Patent Application Publication No. 2016/0029685, entitled: "Microwave Sterilization for Pasteurization." In particular, a conveyor belt or chain driven mechanism can include a belt driven by a motor (not shown) or other suitable types of actuators. Additionally, grasping mechanisms along the side of the transport carriers can also be utilized to carry such transport carriers 108 to destinations along the processing system shown in FIG. 1.

It is to be noted that using the configurations herein, a target heating profile may be achieved by selecting a material of construction for the individual transport carriers (e.g., 108 (FIG. 10A and FIG. 10B), 408 (FIG. 11), 410 (FIG. 12)), as discussed above. Moreover, a heating pattern can be, for example, determined by monitoring a color profile of a simulated composition in a sectional, layered, or another determined manner. In other embodiments, the heating pattern can also be determined by monitoring a profile in viscosity, gelation, and/or other characteristics of a simulated composition.

Figure 13:
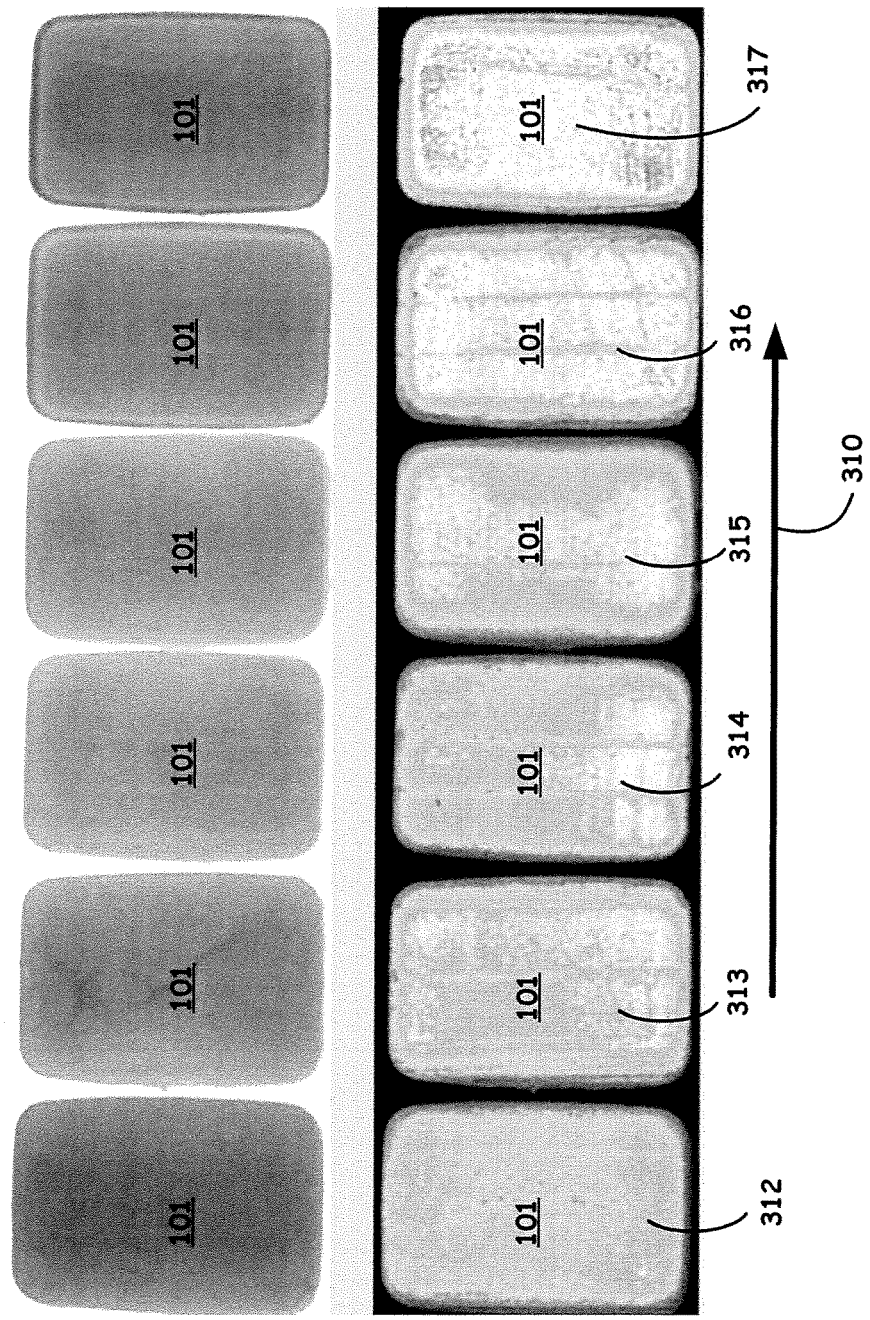
FIG. 13 shows a heating pattern for the middle layer of a 10 ounce packaged item moving along a direction in a processing system and utilized in a transport carrier, as disclosed herein.

Accordingly, FIG. 13 shows a heating pattern for the middle layer of a 10 ounce packaged item 101 moving along a direction 310 (also denoted with an arrow) in the processing system 100 (FIG. 1). Thus, using example carrier transport embodiments disclosed herein, the top row shows an image of 10 ounce packaged item 101 along the heating travel with the bottom row showing a corresponding color profile (shown herein in grey scale) 312, 313, 314, 315, 316, and 317, so as to better depict heating uniformity during the process. While color better illustrates the overall capability of the system 100 (FIG. 1) that incorporates a transport carrier 108 as disclosed herein, it nonetheless illustrates a generally and substantially uniform heating profile of item 101 via the resultant substantially brightened areas in the item 101 shown at the 317 position of travel.

Figure 14:
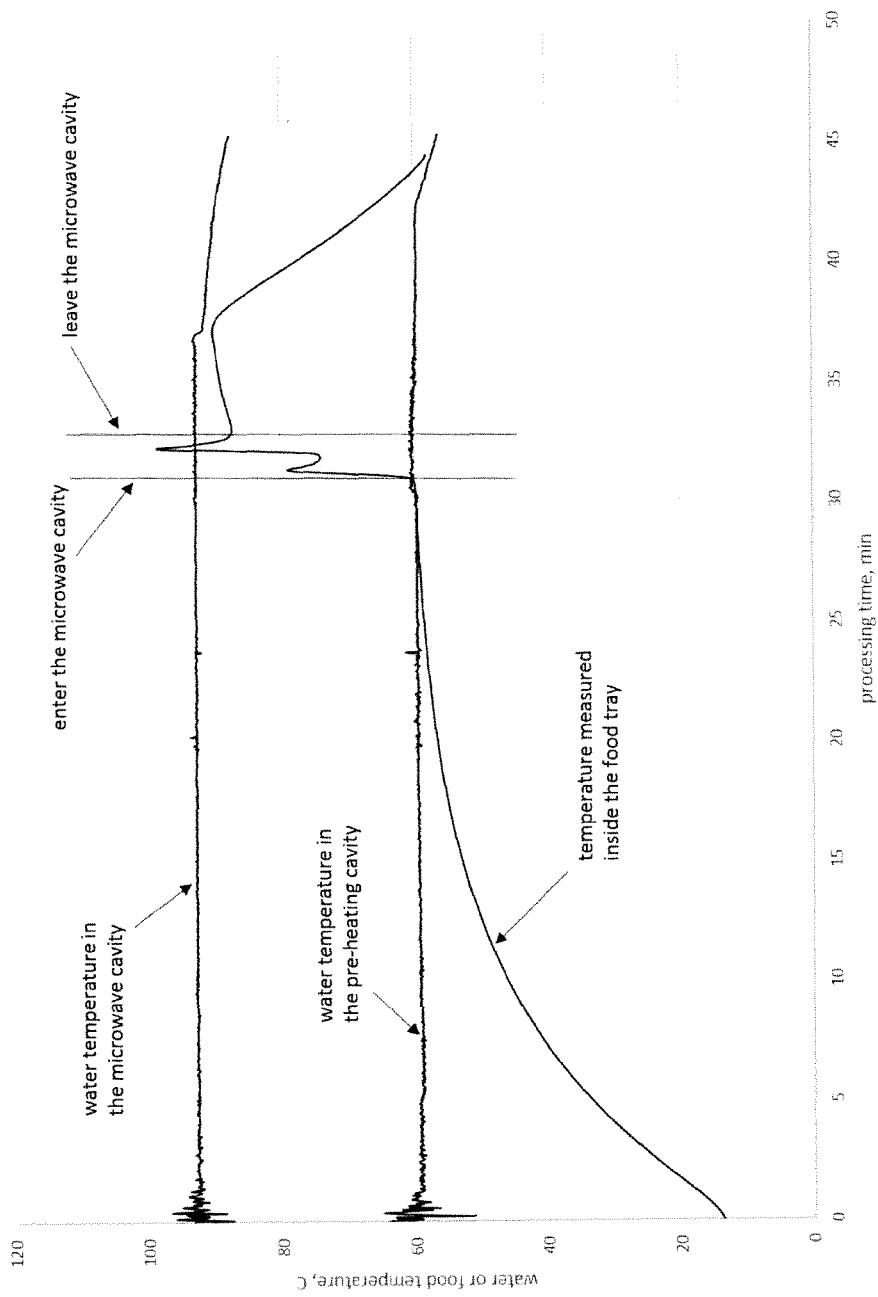
FIG. 14 shows Graphs of a temperature profile measured by wireless data logger at the location of cold spot inside the 10-oz food tray.

To supplement the imaging shown in FIG. 13, FIG. 14 shows Graphs of a temperature profile measured by wireless data logger at the location of the cold spot inside the 10-oz food tray. The temperature plot shows the food tray was heated up to about 60 degrees C. via the immersion fluid in the preheating section. At about 31 minutes along the carrier travel and as it enters the microwave cavity region, it rapidly gets heated to a peak of about 98 degrees C. At 33 minutes it leaves the microwave cavity and enters the holding section, then cools down to the temperature of the surrounding immersion fluid wherein at 37.4 minutes it enters the cooling section to enable the temperature to equilibrate to room temperature.

Figure 15:
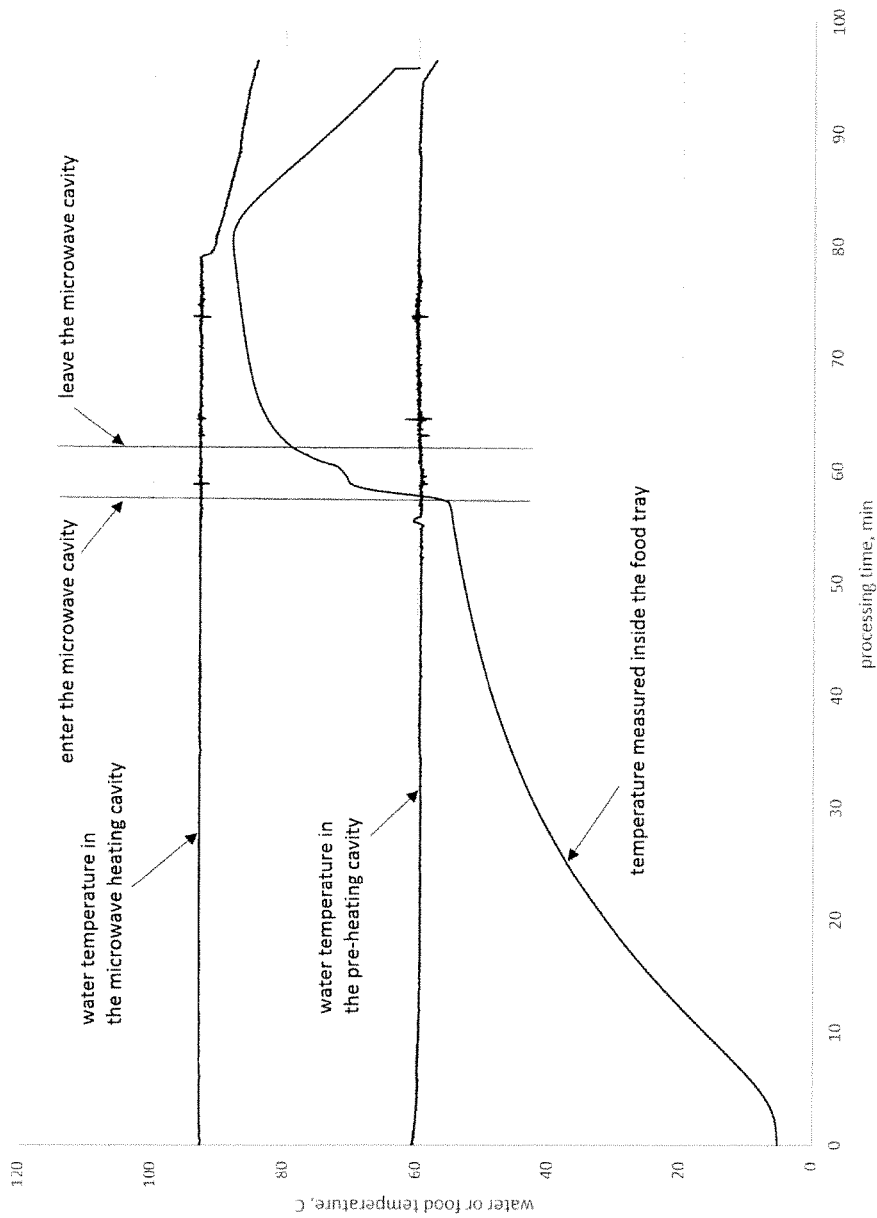
FIG. 15 show a temperature profile measured by wireless data logger at the location of cold spot inside of a 6 pound food tray.

Moreover, the graphs in FIG. 15 show a temperature profile measured by wireless data logger at the location of the cold spot inside of a 6 pound food tray. The temperature plot shows the food tray heated up to about 57 degrees C. via the immersion fluid in the preheating section. At about 55 minutes along the carrier travel and as it enters the microwave cavity region, it rapidly gets heated to a peak of about 79 degrees C. At 62 minutes it leaves the microwave cavity and enters the holding section, then cools down to the temperature of the surrounding immersion fluid wherein at 79.5 minutes it enters the cooling section to enable the temperature to equilibrate to room temperature.

It is to be understood that features described with regard to the various embodiments herein may be mixed and matched in any combination without departing from the spirit and scope of the invention. Although different selected embodiments have been illustrated and described in detail, it is to be appreciated that they are exemplary, and that a variety of substitutions and alterations are possible without departing from the spirit and scope of the present invention.

We claim:

1. A transport carrier for carrying one or more food items to be sterilized or pasteurized with microwave energy, the transport carrier comprising:
    a rectangular carrier base configured for being transported on a conveyor, the carrier base having a first end opposite a second end and a first side opposite a second side, wherein the first side and the second side each extend between the first end and the second end;
    one or more cross members coupled to and extending between the first side and the second side of the carrier base; and
    a tray member comprising at least one material of construction selected from a metal, a metal alloy, and a plastic,
    wherein the tray member extends between the first end and the second end and along the first side and the second side of the carrier base, and
    wherein the tray member comprises one or more apertures configured to receive one or more food items to be sterilized or pasteurized with microwave energy while immersed in an immersion fluid, and
    wherein the tray member comprises a plurality of ancillary apertures of one or more shapes and sizes for transport of the immersion fluid therethrough, wherein the plurality of ancillary apertures are configured to reduce an amount of material utilized in the tray member so as to enable an overall reduction of weight for the transport carrier,
    wherein said plurality of ancillary apertures are different from said one or more apertures configured to receive said one or more food items to be sterilized or pasteurized with microwave energy.

2. The transport carrier of claim 1, wherein the tray member is configured as a plate that is removeably coupled to the transport carrier.

3. The transport carrier of claim 1, wherein the carrier base comprises a plurality of fluid channels for transport of the immersion fluid therethrough, wherein the plurality of fluid channels are further configured to reduce an amount of material utilized in the carrier plate so as to enable an overall reduction of weight for the transport carrier.

4. The transport carrier of claim 1, wherein the carrier base and the one or more cross members comprises at least one material of construction selected from a metal, a metal alloy, and a plastic material.

5. The transport carrier of claim 2, wherein the plate is selected from a plurality of individually designed plates, and wherein the one or more apertures provided by each of the individually designed plates further comprises a shape and a size configured to receive the one or more items having similarly configured one or more sizes and shapes.

6. The transport carrier of claim 5, wherein the carrier base is configured to receive a plurality of the individually designed plates extending in a coupled parallel configuration between the first side and the second side.

7. The transport carrier of claim 5, wherein the carrier base comprises a plurality of longitudinally coupled carrier bases, wherein each of the longitudinally coupled carrier bases is configured to receive an individually designed plate that extends between the first side and the second side of respective each of the longitudinally coupled carrier base.

* * * * *